(12) United States Patent
Pschirer et al.

(10) Patent No.: US 8,083,971 B2
(45) Date of Patent: Dec. 27, 2011

(54) USE OF RYLENE DERIVATIVES AS ACTIVE COMPONENTS IN SOLAR CELLS AND PHOTODETECTORS

(75) Inventors: Neil Gregory Pschirer, Mainz (DE); Ruediger Sens, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/668,975

(22) PCT Filed: Jul. 21, 2008

(86) PCT No.: PCT/EP2008/059502
§ 371 (c)(1),
(2), (4) Date: Jan. 13, 2010

(87) PCT Pub. No.: WO2009/013258
PCT Pub. Date: Jan. 29, 2009

(65) Prior Publication Data
US 2010/0207072 A1    Aug. 19, 2010

(30) Foreign Application Priority Data
Jul. 23, 2007 (EP) .................... 07112969

(51) Int. Cl.
*H01B 1/00* (2006.01)
*H01L 31/00* (2006.01)
*H01L 29/08* (2006.01)
*C07D 221/18* (2006.01)

(52) U.S. Cl. ............ 252/500; 136/263; 257/40; 546/26
(58) Field of Classification Search .................. 252/500; 136/263; 257/40; 546/26
See application file for complete search history.

(56) References Cited

U.S. PATENT DOCUMENTS

| | | | |
|---|---|---|---|
| 4,254,108 A | 3/1981 | Sestanj | |
| 4,927,721 A | 5/1990 | Gratzel et al. | |
| 5,350,644 A | 9/1994 | Graetzel et al. | |
| 5,508,137 A * | 4/1996 | Langhals | 430/78 |
| 6,359,211 B1 | 3/2002 | Spitler et al. | |
| 2005/0098726 A1 | 5/2005 | Peumans et al. | |
| 2005/0224905 A1 | 10/2005 | Forrest et al. | |
| 2008/0269482 A1 | 10/2008 | Pschirer et al. | |
| 2010/0059716 A1 | 3/2010 | Qu et al. | |
| 2010/0072438 A1 | 3/2010 | Qu et al. | |

FOREIGN PATENT DOCUMENTS

| | | |
|---|---|---|
| EP | 1 176 646 | 1/2002 |
| JP | 04 045167 | 2/1992 |
| JP | 10 189065 | 7/1998 |
| JP | 10 334954 | 12/1998 |
| JP | 2000 100484 | 4/2000 |
| JP | 2000 243463 | 9/2000 |
| JP | 2001 93589 | 4/2001 |
| WO | 2004 083958 | 9/2004 |
| WO | 2006 117383 | 11/2006 |
| WO | 2007 006717 | 1/2007 |
| WO | 2007 054470 | 5/2007 |

OTHER PUBLICATIONS

STN Registry No. 1212926-88-7 (Jul. 18, 2011) and 142906-31-8 (Aug. 12, 1992).*
Patsenker, L. D. et al., "Molecular Structure and Spectral Properties of Thionaphthalimides", Journal of Molecular Structure, vol. 655, pp. 311-320 (2003).
Mercadante, R. et al., "Molecular Orbital Calculations of Perylenetetracarboxylic Monoimide and Bisimide. Alkyl Derivatives and Heteroatom Analogs", Journal of Molecular Structure (Theochem), vol. 394 pp. 215-226 (1997).
Gustav, K. et al., "Theoretical Investigations on Absorption and Fluorescence of Perylene and Its Tetracarboxylic Derivatives", Monatshefte Fuer Chemie, vol. 128, pp. 105-112 (1997).
Lakshgmikantham, M. V. et al, "Thioanhydrides. 3, Synthesis, Properties, and Diels-Alder Reactions of Sulfur Analogues of 1,8-Naphthalic Anhydride", J. Org. Chem., vol. 54, No. 20, pp. 4746-4750 (1989).
El-Sharief, A. M. Sh. et al., "A Comparative Study of the Reactions of Phthalides, Naphthalides & Related Compounds", Indian Journal of Chemistry, vol. 20B, pp. 456-459 (Jun. 1981).
Huang, et al., "General Synthesis of Thioxo-1-8-Naphthalimides Via Thioxo-1-8-Naphthalenic Anhydrides", Synthesis, vol. 7, pp. 1109-1111 (1999) XP 002506399.
Orzeszko, A. et al., "Investigation of the Thionation Reaction of Cyclic Imides", Zeitschrift Fuer Naturforschung, vol. 56b, pp. 1035-1040 (2001).
U.S. Appl. No. 12/296,312, filed Oct. 7, 2008, Koenemann, et al.
U.S. Appl. No. 12/670,036, filed Jan. 21, 2010, Pschirer, et al.
U.S. Appl. NO. 12/668,299, filed Jan. 8, 2010, Klaus, et al.
U.S. Appl. No. 12/738,947, filed Apr. 20, 2010, Koenemann, et al.

* cited by examiner

*Primary Examiner* — Mark Kopec
*Assistant Examiner* — Jaison Thomas
(74) *Attorney, Agent, or Firm* — Oblon, Spivak, McClelland, Maier & Neustadt, L.L.P.

(57) ABSTRACT

The invention relates to compounds of general formula (I) and to the use thereof as active materials in solar cells and photodetectors. The variables in formula (I) are defined in the specification. Formula (I) also has the following example.

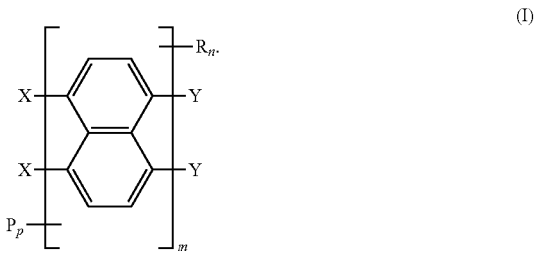

(I)

5 Claims, No Drawings

USE OF RYLENE DERIVATIVES AS ACTIVE COMPONENTS IN SOLAR CELLS AND PHOTODETECTORS

The present invention relates to the use of compounds of the general formula (I)

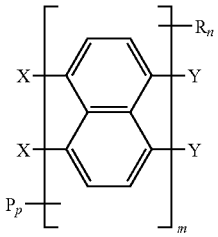

(I)

in which the variables are each defined as follows:
X are joined to one another with formation of a six-membered ring to give a radical of the formula (x1), (x2) or (x3)

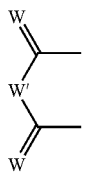

(x1)

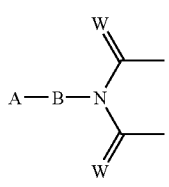

(x2)

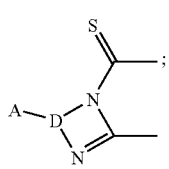

(x3)

both are each a —CWWM radical;
Y one of the two radicals is either a radical of the formula (y1)

-L-NR$^1$R$^2$ (y1)

or a radical of the formula (y2)

-L-Z—R$^3$ (y2)

and the other radical is hydrogen;
are joined to one another with formation of a six-membered ring to give a radical of the formula (y3) or (y4)

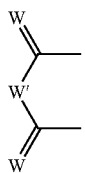

(y3)

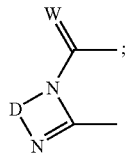

(y4)

or both are hydrogen;
W are each independently O or S;
W' is O, S or N—R',
with the proviso that at least one of the variables W or W in the general formula I is defined as S;
R are identical or different radicals:
aryloxy, arylthio, hetaryloxy or hetarylthio, to each of which may be fused further saturated or unsaturated 5- to 7-membered rings whose carbon skeleton may be interrupted by one or more nonadjacent —O—, —S—, —NR$^4$—, —N=CR$^4$—, —CO—, —SO— and/or —SO$_2$— moieties, where the entire ring system may be mono- or polysubstituted by the following (i), (ii), (iii), (iv) and/or (v) radicals:
(i) C$_1$-C$_{30}$-alkyl whose carbon chain may be interrupted by one or more nonadjacent —O—, —S—, —NR$^4$—, —N=CR$^4$—, —C≡C—, —CR$^4$=CR$^4$—, —CO—, —SO— and/or —SO$_2$— moieties and which may be mono- or polysubstituted by: C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl and/or saturated or unsaturated C$_4$-C$_7$-cycloalkyl whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the (het)aryl and cycloalkyl radicals may each be mono- or polysubstituted by C$_1$-C$_{18}$-alkyl and/or the above radicals mentioned as substituents for alkyl;
(ii) C$_3$-C$_8$-cycloalkyl whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties and to which may be fused further saturated or unsaturated 5- to 7-membered rings whose carbon skeleton may be interrupted by one or more nonadjacent —O—, —S—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$; —COOR$^7$, —SO$_3$R$^7$, —PR$^7{}_2$ and/or —POR$^7$R$^7$;
(iii) aryl or hetaryl, to which may be fused further saturated or unsaturated 5-7-membered rings whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl, (het)aryloxy and/or (het)arylthio, where the (het)aryl radicals may each be mono- or polysubstituted by C$_1$-C$_{18}$-alkyl, C$_1$-C$_{12}$-alkoxy, C$_1$-C$_6$-alkylthio, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7_2$, —POR$^7$R$^7$;

(iv) a —U-aryl radical which may be mono- or polysubstituted by the above radicals mentioned as substituents for the aryl radicals (iii), where U is an —O—, —S—, —NR$^4$—, —CO—, —SO— or —SO$_2$— moiety;

(v) C$_1$-C$_{12}$-alkoxy, C$_1$-C$_6$-alkylthio, —C≡CR$^4$, —CR$^4$=CR$^4_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7_2$ and/or —POR$^7$R$^7$;

P is an amino radical —NR$^1$R$^2$;

B is C$_1$-C$_6$-alkylene, phenylene or combinations of these bridging members, where the phenylene radicals may be mono- or polysubstituted by C$_1$-C$_{12}$-alkyl, nitro, cyano and/or halogen;

A is —COOM, —SO$_3$M or —PO$_3$M$_2$;

D is 1,2-phenylene, 1,2- or 2,3-naphthylene or 2,3- or 3,4-pyridylene, each of which may be mono- or polysubstituted by C$_1$-C$_{12}$-alkyl, C$_1$-C$_{12}$-alkoxy, hydroxyl, nitro and/or halogen;

M is hydrogen, an alkali metal cation or [NR$^5$]$_4^+$;

L is a chemical bond or an arylene or hetarylene radical which is bonded to the rylene skeleton directly or via ethenylene or ethynylene and is of the formulae —Ar—  —Ar-E-Ar— in which the (het)arylene radicals Ar may be the same or different, may comprise heteroatoms as ring atoms and/or may comprise fused saturated or unsaturated 5- to 7-membered rings which may likewise comprise heteroatoms, where the entire ring system may be mono- or polysubstituted by phenyl, C$_1$-C$_{12}$-alkyl, C$_1$-C$_{12}$-alkoxy, C$_1$-C$_{12}$-alkylthio and/or —NR$^5$R$^6$;

E is a chemical bond or an —O—, —S—, —NR$^4$—, —C≡C—, —CR$^4$=CR$^4$— or C$_1$-C$_6$-alkylene moiety;

R$^1$, R$^2$ are each independently one of the alkyl radicals (i), cycloalkyl radicals (ii) or (het)aryl radicals (iii) mentioned as substituents for the R radicals; joined to one another to form a saturated or unsaturated, 5- to 7-membered ring which comprises the nitrogen atom and whose carbon chain may be interrupted by one or more nonadjacent —O—, —S— and/or —NR$^4$-moieties, to which may be fused one or two unsaturated or saturated 4- to 8-membered rings whose carbon chain may likewise be interrupted by these nonadjacent moieties and/or —N=, where the entire ring system may be mono- or polysubstituted by: C$_1$-C$_{24}$-alkyl which may be substituted by C$_1$-C$_{18}$-alkoxy, C$_1$-C$_{18}$-alkylthio and/or —NR$^5$R$^6$, (het)aryl which may be mono- or polysubstituted by C$_1$-C$_{18}$-alkyl and/or the above radicals mentioned as substituents for alkyl, C$_1$-C$_{18}$-alkoxy, C$_1$-C$_{18}$-alkylthio and/or —NR$^5$R$^6$;

Z is —O— or —S—;

R$^3$ is one of the alkyl radicals (i) or (het)aryl radicals (iii) mentioned as substituents for the R radicals;

R' is hydrogen;
C$_1$-C$_{30}$-alkyl whose carbon chain may be interrupted by one or more nonadjacent —O—, —S—, —NR$^4$—, —N=CR$^4$—, —C≡C—, —CR$^4$=CR$^4$—, —CO—, —SO— and/or —SO$_2$— moieties and which may be mono- or polysubstituted by the (ii), (iii), (iv) and/or (v) radicals mentioned as substituents for the R radicals;

C$_3$-C$_8$-cycloalkyl to which may be fused further saturated or unsaturated 5- to 7-membered rings whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the entire ring system may be mono- or polysubstituted by the (i), (ii), (iii), (iv) and/or (v) radicals mentioned as substituents for the R radicals; aryl or hetaryl, to which may be fused further saturated or unsaturated 5- to 7-membered rings whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the entire ring system may be mono- or polysubstituted by the (i), (ii), (iii), (iv), (v) radicals mentioned as substituents for the R radicals, and/or aryl- and/or hetarylazo which may each be substituted by C$_1$-C$_{10}$-alkyl, C$_1$-C$_6$-alkoxy and/or cyano;

R$^4$ is hydrogen or C$_1$-C$_{18}$-alkyl, where the R$^4$ radicals may be the same or different when they occur more than once;

R$^5$, R$^6$ are each independently:
hydrogen;
C$_1$-C$_{18}$-alkyl whose carbon chain may be interrupted by one or more nonadjacent —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^8$;
aryl or hetaryl, to each of which may be fused further saturated or unsaturated 5- to 7-membered rings whose carbon skeleton may be interrupted by one or more nonadjacent —O—, —S—, —CO— and/or —SO$_2$— moieties, where the entire ring system may be mono- or polysubstituted by C$_1$-C$_{12}$-alkyl and/or the above radicals mentioned as substituents for alkyl, where the R$^5$ radicals may be the same or different when they occur more than once;

R$^7$ is C$_1$-C$_{18}$-alkyl whose carbon chain may be interrupted by one or more nonadjacent —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^8$;
aryl or hetaryl, to each of which may be fused further saturated or unsaturated 5- to 7-membered rings whose carbon skeleton may be interrupted by one or more nonadjacent —O—, —S—, —CO— and/or —SO$_2$— moieties, where the entire ring system may be mono- or polysubstituted by C$_1$-C$_{12}$-alkyl and/or the above radicals mentioned as substituents for alkyl, where the R$^7$ radicals may be the same or different when they occur more than once;

R$^8$ is C$_1$-C$_{18}$-alkyl;

R$^9$, R$^{10}$ are each independently C$_1$-C$_{30}$-alkyl whose carbon chain may be interrupted by one or more nonadjacent —O—, —S—, —NR$^4$—, —N=CR$^4$—, —C≡C—, —CR$^4$=CR$^4$—, —CO—, —SO— and/or —SO$_2$— moieties and which may be mono- or polysubstituted by: C$_1$-C$_{12}$-alkoxy, C$_1$-C$_6$-alkylthio, —C≡CR$^4$, —CR$^4$=CR$^4_2$, hydroxyl, —NR$^5$R$^6$, —NR$^5$COR$^6$, (het)aryl and/or saturated or unsaturated C$_4$-C$_7$-cycloalkyl whose carbon skeleton may be interrupted by one or more nonadjacent —O—, —S—, —NR$^4$—, —N=CR$^4$— and/or —CR$^4$=CR$^4$— moieties, where the (het)aryl and cycloalkyl radicals may each be mono- or polysubstituted by C$_1$-C$_{18}$-alkyl and/or the above radicals mentioned as substituents for alkyl;
aryl or hetaryl, to which may be fused further saturated or unsaturated 5- to 7-membered rings whose carbon skeleton may be interrupted by one or more nonadjacent —O—, —S—, —NR$^4$—, —N=CR$^4$—, —CR⁴=CR⁴—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴=CR⁴$_2$, hydroxyl, —NR⁵R⁶, —NR⁵COR⁶, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, hydroxyl, NR⁵R⁶ and/or —NR⁵COR⁶;

joined to the nitrogen atom to form a saturated or unsaturated, 5- to 7-membered ring whose carbon chain may be interrupted by one or more nonadjacent —O—, —S— and/or —NR⁴-moieties, to which may be fused one or two unsaturated or saturated 4- to 8-membered rings whose carbon chain may likewise be interrupted by these nonadjacent moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —NR⁵R⁶, (het)aryl which may be mono- or polysubstituted by $C_1$-$C_{18}$-alkyl and/or the above radicals mentioned as substituents for alkyl, or $C_1$-$C_{18}$-alkoxy, $C_1$-$C_{18}$-alkylthio and/or —NR⁵R⁶;

m is 1, 2, 3 or 4;

n is 0, 2 or 4 when m=1, 2 or 3;
    is 0, 2, 4 or 6 when m=4;

p is 0, 2 or 4 when m=1, 2 or 3, where n+p=0, 2 or 4;
    is 0, 2, 4 or 6 when m=4, where n+p=0, 2, 4 or 6, as active materials in solar cells or photodetectors.

The present invention further relates to the use of mixtures comprising, as components, K1) compounds of the general formula (I) as electron donors or electron acceptors and K2) one or more compounds which, with respect to component K1, act correspondingly as electron acceptors or electron donors for producing photoactive layers for solar cells or photodetectors.

The present invention further relates to the use of compounds of the general formula (I) as photosensitizers in solar cells or photodetectors.

The present invention also relates to solar cells and photodetectors which comprise compounds of the formula (I) or the aforementioned mixtures, and to compounds of the general formula (I) and the aforementioned mixtures.

The direct conversion of solar energy to electrical energy in solar cells is based on the internal photoeffect of a semiconductor material, i.e. the generation of electron-hole pairs through absorption of photons and the separation of the negative and positive charge carriers at a p-n junction or a Schottky contact. The photovoltage thus generated can bring about a photocurrent in an external circuit, through which the solar cell releases its power.

The semiconductor can absorb only those photons which have an energy which is greater than its band gap. The size of the semiconductor band gap thus determines the proportion of sunlight which can be converted to electrical energy.

Solar cells which are based on crystalline silicon were produced as early as in the 1950s. At that time, the technology was promoted by the application in space satellites. Even though silicon-based solar cells now dominate the terrestrial market, this technology still remains expensive. Attempts are therefore being made to develop new approaches which are less expensive. Some of these approaches will be outlined hereinafter, which constitute the basis of the present invention.

Dye-Sensitized Solar Cells (DSSCs)

Thin layers or films of metal oxides constitute inexpensive solid semiconductor materials (n-semiconductors), but their absorption, owing to large band gaps, is typically not in the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the charge band of the semiconductor. With the aid of a redox system additionally present in the cell, which is reduced at the counterelectrode, electrons are returned to the sensitizer which is thus regenerated.

Of particular interest for use in solar cells are the semiconductors zinc oxide, tin oxide and especially titanium dioxide, which are used in the form of nanocrystalline porous layers. These layers have a high surface area which is coated with the sensitizer, such that a high absorption of the sunlight is achieved.

DSSCs are one of the most efficient alternative solar cell technologies to date. In a liquid version of this technology, efficiencies of up to 11% are currently being achieved (see, for example, Grätzel M. et al., J. Photochem. Photobio. C, 2003, 4, 145; Chiba et al., Japanese Journal of Appl. Phys., 2006, 45, L638-L640). However, the DSSCs constructed with liquid electrolyte in many cases suffer from suboptimal sealing, which can lead to stability problems. The liquid electrolyte can, however, be replaced by a solid p-semiconductor. The efficiency of the solid version of the dye-sensitized solar cell is currently from approx. 4.6 to 4.7% (Snaith, H., Angew. Chem. Int. Ed., 2005, 44, 6413-6417).

Various inorganic p-semiconductors such as CuI, CuBr.3 $(S(C_4H_9)_2)$ or CuSCN have been used to date in solid dye-sensitized solar cells. In nature too, it is the Cu(I) enzyme plastocyanin which, in photosystem I, reduces the oxidized chlorophyll dimer again. Such p-semiconductors can be processed via at least three different methods, specifically: from solution, by electrodeposition or by laser deposition.

However, problems can arise in practice with the stability of the p-semiconductors, which arise especially as a result of excessively large semiconductor crystals and poor contact to the dye. One approach to preventing this consists in a CuI solution in an organic solvent with the addition of an ionic liquid as a crystallization inhibitor. In this, case, various crystallization inhibitors can be used (usually thiocyanate salts), which allows efficiencies up to 3.75% to be achieved. In other research studies, a ZnO-covered nanoporous $TiO_2$ layer was used in conjunction with CuI and 1-methyl-3-ethylimidazolium thiocyanate (MEISCN). These dye-sensitized solar cells exhibited an efficiency of 3.8%. When $TiO_2$ is covered with MgO and CuI is used (as a p-conductor) with triethylamine hydrothiocyanate (as a crystallization inhibitor), it is possible to achieve efficiencies of up to 4.7%. CuSCN can also be used as a solid p-semiconductor from a solution and exhibits an efficiency of about 2%. Electrochemical deposition should enable better penetration into the mesoporous pores when the p-semiconductor can be deposited at negative potentials. In this method, solid dye solar cells provide efficiencies of 1.5%, even though only approx. 12% of the incident light is generally absorbed owing to a relatively thin ZnO layer. Finally, laser deposition produces relatively small grains, which leads to a very good short-circuit current $I_{SC}$ of approx. 12.2 mA/cm² in spite of an about 10 μm-thick $TiO_2$ layer, and an efficiency of approx. 2.8% at an active area of approx. 1 cm².

Organic polymers have also already been used as solid p-semiconductors. Examples thereof include polypyrrole, poly(3,4-ethylenedioxythiophene), carbazole-based polymers, polyaniline, poly(4-undecyl-2,2'-bithiophene), poly(3-octylthiophene), poly(triphenyldiamine) and poly(N-vinylcarbazole). In the case of poly(N-vinylcarbazole), the efficiencies reach up to 2%. Even a PEDOT (poly(3,4-ethylenedioxythiophene)) polymerized in situ has an efficiency of 0.53%. The polymers described here are typically not used in pure form but rather with additives.

Low molecular weight organic p-semiconductors can likewise be used. The first use of a low molecular weight p-semiconductor in solid dye-sensitized solar cells replaced the liquid electrolyte with a layer of triphenylamine (TPD) applied by vapor deposition. The use of the organic compound 2,2',7,7'-tetrakis(N,N-di-p-methoxyphenylamine)-9,9'-spirobifluorene (spiro-MeOTAD) in dye-sensitized solar cells was reported in 1998. It can be introduced from a solution and has a relatively high glass transition temperature, which prevents undesired crystallization and poor contact to the dye. The methoxy groups adjust the oxidation potential of the spiro-MeOTAD, such that the Ru complex can be regenerated efficiently. When the spiro-MeOTAD alone is used as a p-semiconductor, a maximum IPCE (incident photon to current conversion efficiency) of 5% was obtained. When $N(PhBr)_3SbCl_6$ (as a dopant) and $Li[(CF_3SO_2)_2N]$ were also used, the IPCE rose to 33%, and the efficiency was 0.74%. The use of tert-butylpyridine as a solid p-semiconductor increases the efficiency to 2.56%, and the open-circuit voltage ($V_{oc}$) was approx. 910 mV and the short-circuit current $I_{SC}$ approx. 5 mA at an active area of approx. 1.07 $cm^2$. Dyes which achieved better coverage of the $TiO_2$ layer and have good wetting on spiro-MeOTAD exhibit efficiencies of more than 4%. Even better efficiencies (approx. 4.6%) were reported when the ruthenium complex was equipped with oxyethylene side chains.

Adv. Mater. 17, p. 813 to 815 (2005) proposes an indoline dye for dye-sensitized solar cells with spirobifluorenes as an amorphous organic p-conductor. This organic dye, which has an extinction coefficient four times higher than a ruthenium complex, exhibits a high efficiency (4.1% at one sun) in solid dye-sensitized solar cells.

Moreover, a design has been presented, in which polymeric p-semiconductors are bonded directly to an Ru dye (Peter, K., Appl. Phys. A 2004, 79, 65).

Durrant et al., Adv. Munc. Mater. 2006, 16, 1832 to 1838 states that, in many cases, the photocurrent is directly dependent on the yield in the hole transfer from the oxidized dye to the solid p-conductor. This depends upon two factors: firstly, on the degree of penetration of the p-conductor into the oxide pores and, secondly, on the thermodynamic driving force for the charge transfer (i.e., in particular, the difference in the free enthalpy $\Delta G$ between dye and p-conductor).

DSSCs which are based on titanium dioxide as the semiconductor material are described, for example, in U.S. Pat. No. 4,927,721, Nature 353, p. 737 to 740 (1991) and U.S. Pat. No. 5,350,644, and also Nature 395, p. 583 to 585 (1998) and EP-A 1 176 646. These solar cells comprise monomolecular films composed of transition metal complexes, especially ruthenium complexes, which are bonded to the titanium dioxide layer via acid groups as sensitizers, and iodine/iodide redox systems present in dissolved form or amorphous organic p-conductors based on spirobifluorenes.

Not least for reasons of cost, metal-free organic dyes have also been proposed repeatedly as sensitizers. For instance, U.S. Pat. No. 6,359,211 describes, for this purpose, cyanine, oxazine, thiazine and acridine dyes which have carboxyl groups bonded via an alkylene radical for fixing to the titanium dioxide semiconductor.

The publications JP-A 10-189065, 2000-243463, 2001-093589, 2000-100484 and 10-334954 describe various perylene-3,4:9,10-tetracarboxylic acid derivatives unsubstituted in the perylene skeleton for use in semiconductor solar cells. Specifically, they are: perylenetetracarboximides which bear carboxyalkyl, carboxyaryl, carboxyarylalkyl or carboxyalkylaryl radicals on the imide nitrogen atoms and/or are imidated with p-diaminobenzene derivatives, in which the nitrogen atom of the amino group is substituted by two further phenyl radicals in the p position or is part of a heteroaromatic tricyclic system; perylene-3,4:9,10-tetracarboxylic monoanhydride monoimides which bear the aforementioned radicals or alkyl or aryl radicals without further functionalization on the imide nitrogen atom, or semicondensates of perylene-3,4:9,10-tetracarboxylic dianhydride with 1,2-diaminobenzenes or 1,8-diaminonaphthalenes which are converted to the corresponding diimides or double condensates by further reaction with primary amine; condensates of perylene-3,4:9,10-tetracarboxylic dianhydride with 1,2-diaminobenzenes which are functionalized by carboxyl or amino radicals; and perylene-3,4:9,10-tetracarboximides which are imidated with aliphatic or aromatic diamines.

New J. Chem. 26, p. 1155 to 1160 (2002) studies the sensitization of titanium dioxide with perylene derivatives which are unsubstituted in the perylene skeleton (bay positions). Specific mention is made of 9-dialkylaminoperylene-3,4-dicarboxylic anhydrides, perylene-3,4-dicarboximides which are 9-substituted by dialkylamino or carboxymethylamino and bear, on the imide nitrogen atom, a carboxymethyl or a 2,5-di(tert-butyl)phenyl radical, and N-dodecylaminoperylene-3,4:9,10-tetracarboxylic monoanhydride monoimide.

Further rylene derivatives suitable for the sensitization are detailed in document WO 2007/054470 A1.

One disadvantage of the DSSCs is that the proportion of light which can be used by the dye is limited by the energetic separation between the Fermi energies of the n- and p-conductors used. The photovoltage is also limited by this separation. Moreover, the DSSCs must be of a relatively thin design (1-2.5 µm) and consequently do not always exploit the entire spectral region of sunlight.

Organic Solar Cells

Photovoltaic elements based on a p-n junction and in which some or even all of the photoactive materials are organic have been known for almost 50 years (see, for example, Kearns, K, Calvin, M., J., Chem. Phys. 1958, 29, 950 to 951). Such elements are designed such that at least one of the semiconductors (n-semiconductor and/or p-semiconductor) absorbs a photon, and the exciton formed is transported to the p-n junction and one or both of the two charges is or are transported from there to the electrode.

Organic solar cells may be composed of low molecular weight compounds (also referred to hereinafter as "low molecular weight cells"), of polymers (also referred to hereinafter as "polymer cells"), of oligomers or of combinations of some or several of these materials. Organic solar cells have at least one acceptor material in which the n-charged transport (electron transport) dominates and which thus constitutes the organic analog to an n-semiconductor, and at least one donor material in which the p-charged transport (hole transport) dominates and which thus constitutes the organic analog to a p-semiconductor. Alternatively or additionally, it is also possible to use inorganic nanoparticles as acceptors (see, for example, Alivisatos A., Science, 2002, 295, 2425 to 2427).

The variety of organic photovoltaic designs can be ordered according to processing methods. The materials are typically applied under reduced pressure (for example by means of physical vapor deposition, PVD, chemical vapor deposition, CVD, molecular beam epitaxy or other processes or process combinations) and/or from a solution (for example by spin-coating, printing or other wet-chemical technologies). Hybrids of these cell types and deposition methods also exist, for example cells with low molecular weight layers applied under reduced pressure, and polymeric layers applied by wet chemical means.

Low molecular weight cells, in which both p- and n-materials are deposited under reduced pressure, have been known for many years (see, for example, Tang, C. W., App. Phys. Lett. 1986, 48, 183). These cells have to date consisted usually of copper phthalocyanine (CuPc) as a donor material and of 3,4,9,10-perylenetetracarboxylic bisimide benzimidazole (PTCBI) or of a fulierene (e.g. $C_{60}$) as an acceptor material. The first cell by Tang exhibited an efficiency of 1%. Cells produced from the same organic materials have in the meantime been improved and reach an efficiency of 2.7% (Peumans et al., Nature of Materials, 2005, 4, 37 to 41). The efficiencies of cells in which $C_{60}$ is used as an acceptor material have in the meantime risen to 5.0%.

For the increase in the efficiencies of organic solar cells, essentially two approaches should be addressed:

In order to utilize substantially all incident photons, relatively high layer thicknesses are used (e.g. 100 nm). To generate electrical current, the excited state generated by the absorbed photons must, however, reach a p-n junction in order to generate the hole and an electron, which then flows to the anode and cathode. Most organic semiconductors, however, have only diffusion lengths for the excited state of up to 10 nm. Even by means of the best production processes known to date, the distance over which the excited state has to be passed on can be deduced only to a minimum of from 10 to 30 nm.

A first approach in organic photovoltaics is therefore in the direction of the so-called "bulk heterojunction": in this case, the photoactive layer comprises the acceptor and donor compound(s) as a bicontinuous phase. By virtue of photoinduced charge transfer from the excited state of the donor compounds to the acceptor compound, owing to the spatial proximity of the compounds, a rapid charge separation compared to other relaxation operations takes place, and the holes and electrons formed are discharged via the corresponding electrodes. Between the electrodes and the photoactive layer, further layers, for example hole or electron transport layers, are often applied in order to increase the efficiency of such cells. The use of doped N,N'-dimethylperylenetetracarboximide ("MPP") as an electron transport material is described, for example, by D. Gebeyehu et al., Solar Energy Materials & Solar Cells 79, 81 to 92, 2003.

In a second approach, an exciton blocking layer (EBL) is used between acceptor layer and cathode. This layer is intended to cause the excitons not to migrate to the cathode, where they would decompose without being utilized at the transition between metal and organic layers. Moreover, these blocking layers also serve as a diffusion barrier against the penetration of the electrode into the photoactive material.

When CuPc is replaced in the Tang cell by SubPc (subphthalocyanine), it is possible to achieve higher photovoltages $V_{OC}$ (up to approx. 0.97 V, cf. Mutolo, K., J. Am. Chem. Soc., 2006, 128, 8108). Other material combinations, such as oligiothiophenes (e.g. α,α'-bis(2,2-dicyanovinyl)quinquethiophene, DCV5T) as a donor material with $C_{60}$ as an acceptor material, also exhibit high efficiencies (e.g. from 3.4 to 3.8%; cf. Schulze et al., Adv. Mater., 2006, 18, 2872 to 2875; Schulze et al., Proc. Of SPIE Vol. 6192, 61920C-1 (2006)). A more recent study uses so-called "triplet" absorbers, which have a high exciton diffusion length (Yang, Y. Adv. Mater., 2005, 17, 2841).

An alternative approach to the use of vacuum processes for the application of low molecular weight substances is the use of soluble low molecular weight compounds which can likewise be applied by wet chemical means in an analogous manner to polymers or oligomers. Cells produced in this way function by the same principle as the low molecular weight cells described above. In this case, p- and n-materials are processed from one or more solutions and/or dispersions. A multitude of such molecules has already been used in such cells, but the efficiencies were to date comparatively low. An improvement in the efficiency can be achieved by thermal treatment (tempering) of the junction (i.e. of the bulk heterojunction), since this improves the arrangement of the molecules. This effect becomes particularly noticeable when the molecules used are thermotropic liquid crystals (cf. Schmidt-Mende, L. et al., Science 2001, 293, 1119 to 1122).

A further concept consists in binding the donor material and the acceptor material covalently in one molecule. A cell type formed in this way, however, has to date exhibited only comparatively low efficiencies (cf. Maggini, M., Chem. Commun., 2002, 2028 to 2029).

Polymer cells function by the same principle as the low molecular weight cells described above. The difference lies in the fact that at least one of the two absorbers (i.e. acceptor material and/or donor material) is a polymer and is therefore generally processed from solution. Examples of usable polymers are the derivatives of poly(p-phenylenevinylene) (PPV), which include, according to the substituents, both donor materials and acceptor materials. A typical example of a polymer which acts as a donor material is MEH-PPV (methylethylhexyl), whereas cyano-substituted PPV (CN-PPV) can act as an acceptor material. Efficiencies of polymer cells formed in this way were in the region of 1%. The systems which have shown the best performances to date consist of P3HT (poly(3-hexylthiophene)) as a donor material and PCBM ([6,6]-phenyl-$C_{61}$-butyric acid methyl ester) as an acceptor material. Solar cells with efficiencies up to between 4.8 and 5.0% are known. Low band gap polymers are also used and exhibit an improved overlap of the absorption with the sun spectrum. Using PCBM, it is possible to achieve efficiencies of approx. 3.2%. In this case, optical spacers are also used in some cases in order to maximize the light absorption in the active layer. App. Phys. Lett, 2001, 78, 841 showed that the influence on the efficiency depends on the processing (for example on the solvent used, etc.). In order to improve the proportion of photons absorbed, new materials are used, for example low band gap polymers (poly[2,6-(4,4-bis(2-ethylhexyl)-4H-cyclopenta[2,1-b;3,4-b']dithiophene)-alt-4,7-(2, 1,3-benzothiadiazole)]), are used together with C71-PCBM, which exhibit an efficiency of up to 5.5%. Polymers are also used as donor materials with materials including perylenes or with inorganic nanorods as acceptor materials, with an efficiency of up to 1.7% in the latter case.

Organic solar cells which are processed from solution have the advantage that they enable a multitude of less expensive production processes which are suitable for a high throughput. For example, it is possible to use printing processes for the production, for instance inkjet printing processes, which also enable structuring of the organic layers.

It was therefore an object of the invention to provide organic compounds which feature advantageous performance properties, especially strong light absorption and high stability, and may find use as active materials in solar cells. In particular, the absorption spectrum should be as wide as possible, be adjustable easily to the requirements and additionally comprise the NIR region.

Accordingly, the use cited at the outset of compounds of the general formula (I)

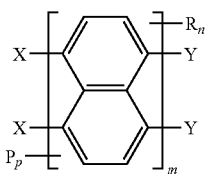
(I)

as active materials in solar cells or photodetectors has been found.

The compounds of the general formula (I) in which both X together are a radical of the formula (x1), (x2) or (x3) and both Y together are a radical of the formula (y3) or (y4) are obtainable in a simple manner from the compounds in which both X together are defined as

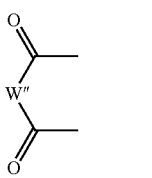
(x1')

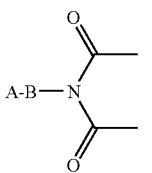
(x2')

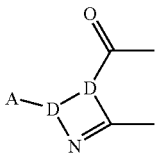
(x3')

and both Y together are defined as

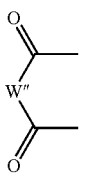
(y3')

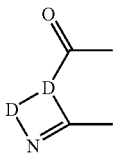
(y4')

where W" is oxygen or an N—R' group. These starting compounds and their preparation are described in documents WO 2006/117383 A1 and WO 2007/006717 A1 and the literature cited therein.

The compounds of the general formula (I) in which both X together are a radical of the formula (x1), (x2) or (x3) and Y is either a radical of the formula (y1)

-L-NR$^1$R$^2$ (y1)

or a radical of the formula (y2)

-L-Z—R$^3$ (y2)

and the other Y radical is hydrogen are obtainable in a simple manner from the compounds in which both X together are defined as one of the (x1'), (x2') or (x3') radicals shown above and Y is either a radical of the formula (y1) or a radical of the formula (y2). Such starting compounds are described in document WO 2007/054470 A1.

Reaction of the corresponding starting compounds with the Davy or Lawesson reagent, depending especially on the reaction time and reaction temperature and the molar ratio of sulfidation reagent to starting compound affords the compounds of the general formula (I) in which one or more of the carbonyl oxygen atoms and/or of the W" group with the definition of oxygen in the x1', x2', x3', y3' and y4' radicals of the starting compounds are replaced by sulfur. The general conditions in the reaction with the Davy or Lawesson reagent are known to those skilled in the art. The more exact conditions can be determined, if appropriate, by means of simple preliminary experiments. For example, reference is made here to the article by A. Orzeszko et al., "Investigation of the Thionation Reaction of Cyclic Imides", Z. Naturforsch. 56 b, 1035 to 1040, 2001, in which the exchange of the carbonyl oxygen for sulfur in cyclic imides is studied.

When, in the general formula (I), one or both X is or are defined as a —CWWM radical, this is a (sulfated) acid radical —CWWH or a corresponding salt of an alkali metal cation, or an NH$_4^+$ or [NR$^5_4$]$^+$ salt with identical or different R$^5$ radicals.

Suitable bridging members B are C$_1$-C$_6$-alkylene radicals and phenylene radicals and combinations of these radicals, for example alkylenephenylene, phenylenealkylene and alkylenephenylenealkylene radicals. The phenylene radicals may each be mono- or polysubstituted by C$_1$-C$_{12}$-alkyl, C$_1$-C$_6$-alkoxy, hydroxyl, nitro, cyano and/or halogen, but are preferably unsubstituted.

The acid groups A are carboxyl, sulfo or phosphonic acid groups, which may likewise be present as a free acid or in salt form.

In the radicals of the formula (x3) which are formed from the radicals of the formula (x3') in the condensation of the dicarboxylic anhydride with an acid-containing o-phenylenediamine, 1,8-diaminonaphthalene or else 3,4-diaminopyridine, and subsequent sulfidation, the acid group A, which may again be present in salt form, is bonded to the aromatic ring system D. The ring system D is otherwise preferably unsubstituted, but may also bear C$_1$-C$_{12}$-alkyl, C$_1$-C$_6$-alkoxy, hydroxyl, nitro and/or halogen as substituents.

Preferred compounds of the formula (I) have, in the 3,4-position, a radical of the formula (x1) or the corresponding dicarboxylic acid salt.

The compounds of the general formula (I) may be unsubstituted at the other end of the molecule (both Y radicals or hydrogen) or be pen-substituted either by a radical of the formula (y1)

-L-NR$^1$R$^2$ (y1)

or a radical of the formula (y2)

in which case the second Y radical is correspondingly hydrogen,
or they comprise the radicals of the formula (y3) or (y4)

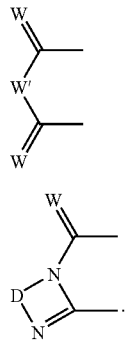

The two Y radicals are correspondingly joined together here to form a six-membered ring.

The bridging member L may be a chemical bond, i.e. the amino group of the (y1) radical or the —Z—$R^3$ moiety of the (y2) radical is bonded directly to the rylene skeleton, or else L may be a (het)arylene radical of the formulae

bonded to the rylene skeleton directly or via ethenylene or ethynylene.

The (het)arylene radicals Ar may comprise heteroatoms as ring atoms and/or fused saturated or unsaturated 5- to 7-membered rings which may likewise comprise heteroatoms. When they are fused ring systems Ar, the bonds to the rylene skeleton and to the functional group may both start from the same ring or from different rings. The entire ring system may additionally be mono- or polysubstituted by phenyl, $C_1$-$C_{12}$-alkyl, $C_1$-$C_{12}$-alkoxy, $C_1$-$C_{12}$-alkylthio and/or —$NR^5R^6$, preference being given to $C_1$-$C_{12}$-alkyl, $C_1$-$C_{12}$-alkoxy and/or —$NR^5R^6$ as substituents.

When the bridging member L comprises two (het)arylene radicals Ar, they are preferably the same, but may also be different. The two Ar radicals may be bonded directly to one another or be linked to one another via an —O—, —S—, —$NR^4$—, —C≡C—, —$CR^4$=$CR^4$— or $C_1$-$C_6$-alkylene moiety. The binding member E is preferably a chemical bond or an —O—, —S—, —$NR^4$— or —C≡C— moiety.

Examples of suitable bridging members L include:
1,4-, 1,3- and 1,2-phenylene, 1,4- and 1,8-naphthylene, 1,4- and 2,3-pyrrylene, 2,5-, 2,4- and 2,3-thienylene, 2,5-, 2,4- and 2,3-furanylene, 2,3-, 2,4-, 2,5-, 2,6-, 3,4- and 3,5-pyridinylene, 2,3-, 2,5-, 2,6-, 3,7-, 4,8-, 5,8- and 6,7-quinolinylene, 2,7-, 3,6-, 4,5-, 2,6-, 3,7-, 4,7- and 4,8-isoquinolinylene, 4,4'-, 3,3'- and 2,2'-biphenylene, 3,3'- and 2,2'-bithienylene, 1,4-[2,5-di(tert-butyl)]phenylene, 1,4-(2,5-dihexyl)phenylene, 1,4-[2,5-di(tert-octyl)]phenylene, 1,4-(2,5-didodecyl)phenylene, 1,4-[2,5-di(2-dodecyl)]phenylene, 4,4'-di(2,2',6,6'-tetramethyl)phenylene, 4,4'-di(2,2',6,6'-tetraethyl)phenylene, 4,4'-di(2,2',6,6'-tetraisopropyl)phenylene, 4,4'-di(2,2',6,6'-tetrahexyl)phenylene, 4,4'-di[2,2',6,6'-tetra(2-hexyl)]phenylene, 4,4'-di[2,2',6,6'-tetra(tert-octyl)]phenylene, 4,4'-di(2,2',6,6'-tetradodecyl)phenylene and 4,4'-di[2,2',6,6'-tetra(2-dodecyl)]phenylene, and also

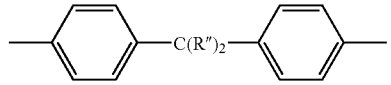

where R'' is hydrogen, methyl, ethyl or phenyl.

Very particularly preferred bridging members L are a chemical bond, 1,4-phenylene, 2,3-thienylene and 4,4'-di(2,2',6,6'-tetramethyl)phenylene.

The $R^1$ and $R^2$ radicals in the amino group of the (y1) radical may each independently be one of the alkyl radicals (i), cycloalkyl radicals (ii) or (het)aryl radicals (iii) mentioned as substituents at the outset for the definition of the variable R. Preferably, the $R^1$ and $R^2$ radicals are especially identical phenyl radicals which may bear, as substituents, $C_1$-$C_{18}$-alkyl, $C_1$-$C_{12}$-alkoxy, $C_1$-$C_6$-alkylthio, —$NR^5R^6$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio, —$NR^5R^6$. They are preferably para-substituted by $C_4$-$C_{18}$-alkyl, especially branched $C_4$-$C_{18}$-alkyl, e.g. tert-octyl, $C_1$-$C_{18}$-alkoxy, e.g. methoxy, or di($C_1$-$C_{18}$-alkyl)amino, e.g. dimethylamino, or unsubstituted.

The $R^1$ and $R^2$ radicals may also be joined to one another to give a saturated or unsaturated, 5- to 7-membered ring which comprises the nitrogen atom of the amino group of the (y1) radical and whose carbon skeleton may be interrupted by one or more nonadjacent —O—, —S— and/or —$NR^4$-moieties ($R^4$: H or $C_1$-$C_{18}$-alkyl, preferably H or $C_1$-$C_6$-alkyl), to which may be fused one or two unsaturated or saturated 4- to 8-membered rings whose carbon chain may likewise be interrupted by these nonadjacent moieties and/or —N═, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the above radicals mentioned as substituents for alkyl, $C_1$-$C_{18}$-alkoxy, $C_1$-$C_{18}$-alkylthio and/or —$NR^5R^6$, preference being given to $C_4$-$C_{18}$-alkyl, $C_1$-$C_{18}$-alkoxy and —$NR^5R^6$ as substituents.

Examples of preferred unsubstituted cyclic amino radicals include piperidyl, pyrrolidyl, piperazyl, morpholinyl, thiomorpholinyl, pyrryl, dibenzopyrryl (carbazyl), dibenzo-1,4-oxiranyl (phenoxazinyl), dibenzo-1,4-thiazinyl (phenothiazinyl), dibenzo-1,4-pyrazyl (phenazinyl) and dibenzopiperidyl, particular preference being given to piperidyl, pyrrolidinyl, dibenzopyrryl, dibenzo-1,4-oxiranyl, dibenzo-1,4-thiazinyl, dibenzo-1,4-pyrazyl and dibenzopiperidyl, particular preference to phenothiazinyl, piperidyl and pyrrolidyl.

The reactants used for these cyclic amino radicals are the corresponding cyclic amines or salts thereof. Examples of suitable substituted and unsubstituted amines include:
piperidine, 2- or 3-methylpiperidine, 6-ethylpiperidine, 2,6- or 3,5-dimethylpiperidine, 2,2,6,6-tetramethylpiperidine, 4-benzylpiperidine, 4-phenylpiperidine, piperidin-4-ol, 2,2,6,6-tetramethylpiperidin-4-ylamine, decahydroquinoline and decahydroisoquinoline;
pyrrolidine, 2-methylpyrrolidine, 2,5-dimethylpyrrolidine, 2,5-diethylpyrrolidine, tropanol, pyrrolidin-3-ylamine, (2,6-dimethylphenyl)pyrrolidin-2-ylmethylamine, (2,6-diisopropyl-phenyl)pyrrolidin-2-ylmethylamine and dodecahydrocarbazole;
piperazine, diketopiperazine, 1-benzylpiperazine, 1-phenethylpiperazine, 1-cyclohexyl-piperazine, 1-phenylpiperazine, 1-(2,4-dimethylphenyl)piperazine, 1-(2-, 3- or 4-methoxyphenyl)piperazine, 1-(2-, 3- or 4-ethoxyphenyl)piperazine, 1-(2-, 3- or 4-fluorophenyl)piperazine, 1-(2-, 3- or 4-chlorophenyl)piperazine, 1-(2-, 3- or 4-bromophenyl)-piperazine, 1-, 2- or 3-pyridin-2-ylpiperazine and 1-benzo[1,3]dioxol-4-ylmethylpiperazine;

morpholine, 2,6-dimethylmorpholine, 3,3,5,5-tetramethylmorpholine, morpholin-2- or -3-ylmethanol, 3-benzylmorpholine, 3-methyl-2-phenylmorpholine, 2- or 3-phenylmorpholine, 2-(4-methoxyphenyl)morpholine, 2-(4-trifluoromethylphenyl)morpholine, 2-(4-chlorophenyl)morpholine, 2-(3,5-dichlorophenyl)morpholine, 3-pyridin-3-ylmorpholine, 5-phenylmorpholin-2-one, 2-morpholin-2-ylethylamine and phenoxazine;

thiomorpholine, 2- or 3-phenylthiomorpholine, 2- or 3-(4-methoxyphenyl)thiomorpholine, 2- or 3-(4-fluorophenyl)thiomorpholine, 2- or 3-(4-trifluoromethylphenyl)thiomorpholine, 2- or 3-(2-chlorophenyl)thiomorpholine, 4-(2-aminoethyl)thiomorpholine, 3-pyridin-3-ylthiomorpholine, 3-thiomorpholinone and 2-phenylthiomorpholin-3-one, and also the thiomorpholine oxides and dioxides.

Examples of particularly preferred radicals of the formula (y1) are:

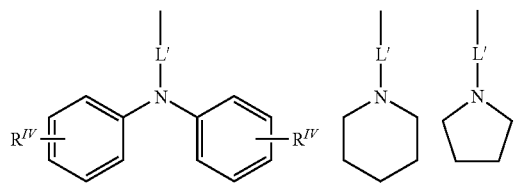

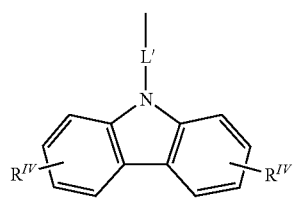

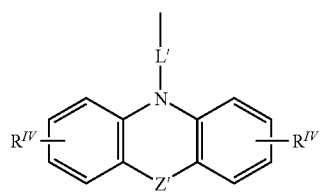

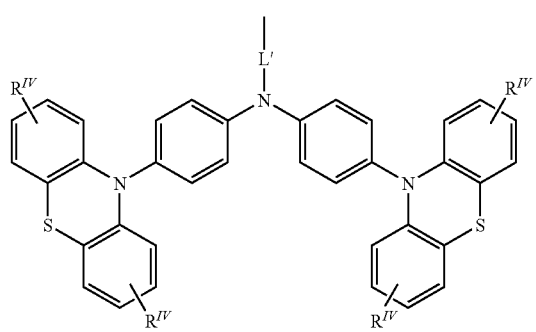

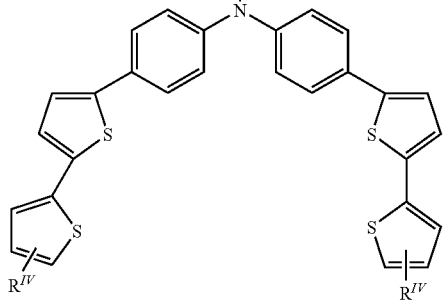

where the variables are defined as follows:
L' is a chemical bond or 1,4-phenylene;
Z' is —O—, —S—, —NR$^{8'}$— or —CH$_2$—, where R$^{8'}$ is C$_1$-C$_{18}$-alkyl;
R$^{IV}$ is C$_4$-C$_{18}$-alkyl, C$_1$-C$_{18}$-alkoxy, (hetero)aryl or —NR$^5$R$^6$.

Very particularly preferred amino groups in the (y1) radicals are the diphenylaminophenylene and especially the diphenylamino radicals detailed above.

For the —Z—R$^3$ moiety of the (y2) radical, particularly preferred bridging members L are a chemical bond, 1,4-phenylene and 2,5-thienylene. A very particularly preferred bridging member L is the chemical bond.

The R$^3$ radical in the —Z—R$^3$ moiety of the (y2) radical may be one of the alkyl radicals (i) or (het)aryl radicals (iii) mentioned as substituents at the outset in the definition of the variable R.

R$^3$ is preferably:
C$_1$-C$_{30}$-alkyl whose carbon chain may be interrupted by one or more nonadjacent —O—, —S— and/or —NR$^4$-moieties and which may be mono- or polysubstituted by: C$_1$-C$_{12}$-alkoxy, hydroxyl and/or aryl which may be mono- or polysubstituted by C$_1$-C$_{18}$-alkyl or C$_1$-C$_6$-alkoxy; phenyl which may be mono- or polysubstituted by: C$_1$-C$_{18}$-alkyl, C$_1$-C$_{12}$-alkoxy, C$_1$-C$_6$-alkylthio, —NR$^5$R$^6$ and/or phenoxy and/or phenylthio, each of which may be mono- or polysubstituted by C$_1$-C$_{18}$-alkyl, C$_1$-C$_{12}$-alkoxy, C$_1$-C$_6$-alkylthio and/or —NR$^5$R$^6$.

Examples of particularly preferred radicals of the formula (y2) are:
phenoxy, phenylthio, naphthyloxy or naphthylthio, each of which may be mono- or polysubstituted by C$_4$-C$_{18}$-alkyl, C$_1$-C$_{18}$-alkoxy and/or —NR$^5$R$^6$.

In the radicals of the formula (y3), in which W' is N—R', R', as well as hydrogen, may be the alkyl radicals (i), cycloalkyl radicals (ii) or (het)aryl radicals (iii) defined at the outset.

R' is preferably defined as follows:
C$_6$-C$_{30}$-alkyl whose carbon chain may be interrupted by one or more nonadjacent —O—, —S— and/or —NR$^4$-moieties and which may be mono- or polysubstituted by: C$_1$-C$_6$-alkoxy, C$_1$-C$_6$-alkylthio, —NR$^9$R$^{10}$ and/or aryl which may be mono- or polysubstituted by C$_1$-C$_{18}$-alkyl or C$_1$-C$_6$-alkoxy, particular preference being given to C$_6$-C$_{30}$ alkyl which is ω-substituted by —NR$^9$R$^{10}$;
(het)aryl, especially phenyl, naphthyl, pyridyl or pyrimidyl, each of which may be mono- or polysubstituted by: C$_1$-C$_{18}$-alkyl, C$_1$-C$_6$-alkoxy, halogen, cyano, nitro, —NR$^9$R$^{10}$, —CONR$^5$R$^6$, —SO$_2$NR$^5$R$^6$ and/or phenoxy, phenylthio, phenylazo and/or naphthylazo, each of which may be substituted by C$_1$-C$_{10}$-alkyl, C$_1$-C$_6$-alkoxy and/or cyano.

R' is most preferably a phenyl radical which is mono- or polysubstituted by $C_1$-$C_{18}$-alkyl or —$NR^9R^{10}$.

The $R^5$ and $R^6$ radicals are each as defined at the outset. They are preferably each independently:

hydrogen;

$C_1$-$C_{18}$-alkyl which may be mono- or polysubstituted by $C_1$-$C_6$-alkoxy, hydroxyl, halogen and/or cyano;

aryl or hetaryl, each of which may be mono- or polysubstituted by $C_1$-$C_6$-alkyl and/or the above radicals mentioned as substituents for alkyl.

Particularly suitable substituents are the alkyl radicals and in particular the amino groups —$NR^9R^{10}$.

The definition of the $R^9$ and $R^{10}$ radicals is likewise specified at the outset. They are preferably each independently:

$C_1$-$C_{30}$-alkyl whose carbon chain may be interrupted by one or more nonadjacent —O—, —S—, —$NR^4$—, —N=$CR^4$—, —C≡C— and/or —$CR^4$=$CR^4$— moieties and which may be mono- or polysubstituted by: $C_1$-$C_{12}$-alkoxy, $C_1$-$C_6$-alkylthio, —C≡$CR^4$, —$CR^4$=$CR^4_2$, hydroxyl, —$NR^5R^6$, —$NR^5COR^6$ and/or (het)aryl which may be mono- or polysubstituted by $C_1$-$C_{18}$-alkyl and/or the above radicals mentioned as substituents for alkyl;

aryl or hetaryl, to which may be fused further saturated or unsaturated 5- to 7-membered rings whose carbon skeleton may be interrupted by one or more nonadjacent —O—, —S—, —$NR^4$—, —N=$CR^4$—, —$CR^4$=$CR^4$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^4$, —$CR^4$=$CR^4_2$, hydroxyl, —$NR^5R^6$, —$NR^5COR^6$, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, hydroxyl, —$NR^5R^6$ and/or —$NR^5COR^6$;

joined to the nitrogen atom to form a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by $C_1$-$C_{24}$-alkyl which may be substituted by $C_1$-$C_{18}$-alkoxy, $C_1$-$C_{18}$-alkylthio and/or —$NR^5R^6$.

The amino groups —$NR^9R^{10}$ are preferably di(het)arylamino groups or cyclic amino groups. Particular preference is given to diphenylamino groups in which the phenyl radicals may be unsubstituted or may have the above substituents, especially the alkyl radicals, preferably in the p-position.

Preferred substitution patterns for the phenyl radicals R' are ortho,ortho'-disubstitution (e.g. alkyl radicals with a secondary carbon atoms in the 1-position) and para-substitution (e.g. alkyl radicals with a tertiary carbon atom in the 1-position and at least 5 carbon atoms or amino groups —$NR^9R^{10}$).

Examples of particularly preferred R' radicals are:

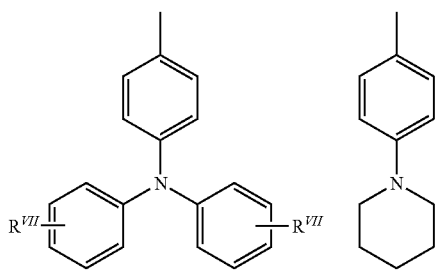

-continued

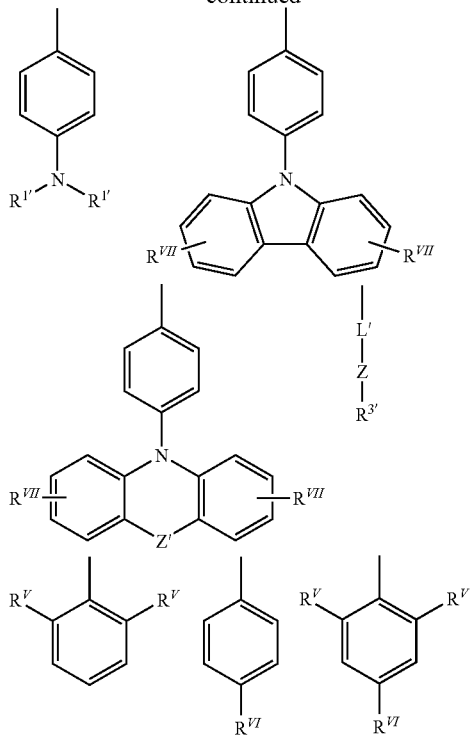

where the variables are defined as follows:

$R^V$ is $C_3$-$C_8$-alkyl with a secondary carbon atom in the 1-position;

$R^{VI}$ is $C_4$-$C_{18}$-alkyl with a tertiary carbon atom in the 1-position or —$NR^9R^{10}$;

$R^{VII}$ is $C_4$-$C_{18}$-alkyl or $C_1$-$C_{18}$-alkoxy;

$R^{1'}$ is $C_1$-$C_{18}$-alkyl;

$R^{3'}$ is phenyl when L' is a chemical bond;

$C_4$-$C_{18}$-alkyl when L' is 1,4-phenylene;

L' is a chemical bond, 1,4-phenylene or 2,5-thienylene;

Z' is —O—, —S—, —$NR^8$— or —$CH_2$—, where $R^8$ is $C_1$-$C_{18}$-alkyl;

Z is —O— or —S—.

Very particularly preferred R' radicals are the diphenylaminophenylene radicals.

The radicals of the formula (y4') in the starting compounds are converted to radicals of the formula (y4) by condensation of the anhydride with aromatic diamines, substituted if desired, especially with o-phenylenediamine or 1,8-diaminonaphthalene or else 3,4-diaminopyridine, and subsequent sulfidation.

Preference is given to compounds of the of the formula (I) in which one of the two Y radicals is either a (y1) or (y2) radical and the other radical is hydrogen, or the two Y radicals together are a (y3) radical where W' is N—R', where the further preferences specified above apply.

Particular preference is given to compounds of the formula (I) in which one of the two Y radicals is either a (y1) or (y2) radical and the other radical is hydrogen.

When the compounds of the formula (I) are to be processed in liquid form or are to be used as photosensitizers, it is advantageous when they are additionally substituted in the aromatic skeleton. Preference is given here to tetrasubstitution in the 1,6,7,12-position in the perylene derivatives (m is 2), 1,6,9,14-position in the terrylene derivatives (m is 3) and 1,6,11,16-position in the quaterrylene derivatives (m is 4). In the perylene and terrylene derivatives, disubstitution in the 1,6- and/or 1,7-position or 1,6- or 9,14-position is also possible, and, in the quaterrylene derivatives, hexasubstitution in the 1,6,8,11,16,18,19-position is also possible. The counting always begins here at the molecule end with the X radicals.

When the compounds of the formula (I) are to be deposited under reduced pressure, which is typically the case in the production of organic solar cells, they may also be unsubstituted in the skeleton, i.e. both n and p in the general formula (I) are each 0.

In general, the starting compounds substituted in the skeleton for the compounds of the formula (I) are present in the form of mixtures of products with different degrees of substitution, in which the tetra- or di- or hexasubstituted products make up the main constituent. Since the substituents are typically introduced by nucleophilic substitution of halogenated, especially brominated, compounds or correspondingly halogenated precursors into the aromatic skeleton, the starting compounds for the compounds of the formula (I) and hence of course also the compounds of the general formula (I) may still comprise traces of halogen, which, if desired, can be removed by transition metal-catalyzed reductive or base-induced dehalogenation.

Suitable substituents R are especially the (het)aryloxy and (het)arylthio radicals defined at the outset. Particularly suitable radicals are phenoxy, thiophenoxy, pyridyloxy, pyrimidyloxy, pyridylthio and pyrimidylthio radicals. The R radicals may corresponds to radicals of the formula (y2).

Preferred R radicals are phenoxy or thiophenoxy radicals, each of which may be mono- or polysubstituted by identical or different (i), (ii), (iii), (iv) and/or (v) radicals:
(i) $C_1$-$C_{30}$-alkyl whose carbon chain may be interrupted by one or more nonadjacent —O—, —S—, —NR$^4$—, —C≡C—, —CR$^4$=CR$^4$— and/or —CO— and/or —SO$_2$— moieties and which may be mono- or polysubstituted by: $C_1$-$C_{12}$-alkoxy, hydroxyl, halogen, cyano and/or aryl which may be mono- or polysubstituted by $C_1$-$C_{18}$-alkyl or $C_1$-$C_6$-alkoxy;
(ii) $C_3$-$C_8$-cycloalkyl whose carbon skeleton may be interrupted by one or more nonadjacent —O—, —S—, —NR$^4$—, —CR$^4$=CR$^4$— and/or —CO— moieties and which may be mono- or polysubstituted by $C_1$-$C_{18}$-alkyl, $C_1$-$C_{12}$-alkoxy and/or $C_1$-$C_6$-alkylthio;
(iii) aryl or hetaryl, to each of which may be fused further 5- to 7-membered saturated or unsaturated rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by: $C_1$-$C_{18}$-alkyl, $C_1$-$C_{12}$-alkoxy, —C≡CR$^4$, —CR$^4$=CR$^4{}_2$, hydroxyl, halogen, cyano, —NR$^9$R$^{10}$, —NR$^5$COR$^6$, —CONR$^5$R$^6$, —SO$_2$NR$^5$R$^6$, —COOR$^7$, —SO$_3$R$^7$, (het)aryl, (het)aryloxy and/or (het)arylthio, where the (het)aryl radicals may each be mono- or polysubstituted by $C_1$-$C_{18}$-alkyl, $C_1$-$C_{18}$-alkoxy and/or cyano;
(iv) a —U-aryl radical which may be mono- or polysubstituted by the above radicals mentioned as substituents for the aryl radicals (iii), where U is an —O—, —S—, —NR$^4$—, —CO—, —SO— or —SO$_2$— moiety;
(v) $C_1$-$C_{12}$-alkoxy, $C_1$-$C_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$ and/or —SO$_3$R$^7$.

The (thio)phenoxy radicals R may be unsubstituted or monosubstituted in the ortho-, meta- or preferably para-position. They may also be di-, tri-, tetra- or pentasubstituted, all substitution patterns being conceivable.

Particularly preferred R radicals are ortho,ortho'-disubstituted (thio)phenoxy radicals of the formula

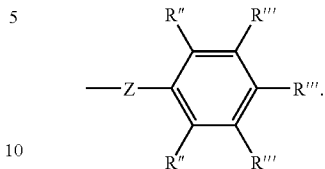

The R" radicals in the two ortho-positions may be the same or different, but they are preferably the same.

The (thio)phenoxy radicals R may also be substituted in one, two or all three further ring positions by identical or nonidentical R'" radicals other than hydrogen.

The (thio)phenoxy radicals R are preferably substituted only in the ortho- and ortho'-position or additionally in the para-position.

In particular, the variables in the abovementioned formula are defined as follows:
Z is —O— or —S—, preferably —O—;
R" are identical or different radicals:
(i) $C_1$-$C_{18}$-alkyl whose carbon chain may be interrupted by one or more —O—, —S—, —NR$^4$— and/or —CO— moieties and which may be mono- or polysubstituted by $C_1$-$C_{12}$-alkoxy, hydroxyl and/or halogen, where no more than one of the R" radicals may have a tertiary carbon atom in the 1-position;
(ii) $C_3$-$C_8$-cycloalkyl which does not comprise a tertiary carbon atom in the 1-position and may be mono- or polysubstituted by $C_1$-$C_{18}$-alkyl and/or $C_1$-$C_{12}$-alkoxy, where no more than one of the R" radicals may have a tertiary carbon atom in the 1-position;
(iii) aryl or hetaryl, each of which may be mono- or polysubstituted by $C_1$-$C_{18}$-alkyl, $C_1$-$C_{12}$-alkoxy, hydroxyl and/or halogen;
(iv) a —U-aryl radical which may be mono- or polysubstituted by the above radicals specified as substituents for the aryl radicals (iii), where U is an —O—, —S— or —NR$^4$— moiety;
(v) $C_1$-$C_{12}$-alkoxy, hydroxyl, halogen or cyano;
R'" are identical or different radicals:
hydrogen;
one of the (i), (ii), (iii), (iv) and (v) radicals mentioned for R", preferably $C_4$-$C_{18}$-alkyl radicals which comprise a tertiary carbon atom in the 1-position or whose carbon chain may be interrupted singly or multiply by —O—, —S— and/or —NR$^4$— and/or which may be mono- or polysubstituted by $C_1$-$C_{12}$-alkoxy, $C_1$-$C_{12}$-alkylthio and/or —NR$^5$R$^6$;
$R^4$ is hydrogen or $C_1$-$C_6$-alkyl.

Specific examples of particularly preferred (thio)phenoxy radicals include:
2,6-dimethylphenoxy, 2,6-diethylphenoxy, 2,6-diisopropylphenoxy, 2,6-di(2-butyl)-phenoxy, 2,6-di(n-butyl)phenoxy, 2,6-di(2-hexyl)phenoxy, 2,6-di(n-hexyl)phenoxy, 2,6-di(2-dodecyl)phenoxy, 2,6-di(n-dodecyl)phenoxy, 2,6-dicyclohexylphenoxy, 2,6-di-methyl-4-(n-butyl)phenoxy, 2,6-diethyl-4-(n-butyl)phenoxy, 2,6-diisopropyl-4-(n-butyl)-phenoxy, 2,6-di(2-butyl)-4-(n-butyl)phenoxy, 2,4,6-tri(n-butyl)phenoxy, 2,6-di(2-hexyl)-4-(n-butyl)phenoxy, 2,6-di(n-hexyl)-4-(n-butyl)phenoxy, 2,6-di(2-dodecyl)-4-(n-butyl)-phenoxy, 2,6-di(n-dodecyl)-4-(n-butyl)phenoxy, 2,6-dicyclohexyl-4-(n-butyl)phenoxy, 2,6-dimethyl-4-(n-nonyl)phenoxy, 2,6-diethyl-4-(n-nonyl)phenoxy, 2,6-diisopropyl-4-(n-nonyl)phenoxy, 2,6-di(2-butyl)-4-(n-nonyl)phenoxy, 2,6-di(2-butyl)-4-(n-nonyl)phenoxy, 2,6-di(2-hexyl)-4-(n-nonyl)phenoxy, 2,6-di(n-hexyl)-4-(n-nonyl)phenoxy, 2,6-di(2-dodecyl)-4-(n-nonyl)phenoxy, 2,6-di(n-dodecyl)-4-(n- nonyl)phenoxy, 2,6-dicyclohexyl-4-(n-nonyl)phenoxy, 2,6-dimethyl-4-(n-octadecyl)phenoxy, 2,6-diethyl-4-(n-octadecyl)-phenoxy, 2,6-diisopropyl-4-(n-octadecyl) phenoxy, 2,6-di(2-butyl)-4-(n-octadecyl)phenoxy, 2,6-di(2-butyl)-4-(n-octadecyl)phenoxy, 2,6-di(2-hexyl)-4-(n-octadecyl)phenoxy, 2,6-di(n-hexyl)-4-(n-octadecyl) phenoxy, 2,6-di(2-dodecyl)-4-(n-octadecyl)phenoxy, 2,6-di(n-dodecyl)-4-(n-octadecyl)phenoxy, 2,6-dicyclohexyl-4-(n-octadecyl)phenoxy, 2,6-dimethyl-4-(tert-butyl)phenoxy, 2,6-diethyl-4-(tert-butyl)phenoxy, 2,6-diisopropyl-4-(tert-butyl) phenoxy, 2,6-di(2-butyl)-4-(tert-butyl)phenoxy, 2,6-di-(n-butyl)-4-(tert-butyl)phenoxy, 2,6-di(2-hexyl)-4-(tert-butyl) phenoxy, 2,6-di(n-hexyl)-4-(tert-butyl)-phenoxy, 2,6-di(2-dodecyl)-4-(tert-butyl)phenoxy, 2,6-di(n-dodecyl)-4-(tert-butyl)-phenoxy, 2,6-dicyclohexyl-4-(tert-butyl)phenoxy, 2,6-dimethyl-4-(tert-octyl)phenoxy, 2,6-diethyl-4-(tert-octyl)phenoxy, 2,6-diisopropyl-4-(tert-octyl)phenoxy, 2,6-di(2-butyl)-4-(tert-octyl)phenoxy, 2,6-di(n-butyl)-4-(tert-octyl)phenoxy, 2,6-di(2-hexyl)-4-(tert-octyl)phenoxy, 2,6-di(n-hexyl)-4-(tert-octyl)phenoxy, 2,6-di(2-dodecyl)-4-(tert-octyl)phenoxy, 2,6-di(n-dodecyl)-4-(tert-octyl)phenoxy and 2,6-dicyclohexyl-4-(tert-octyl)phenoxy;

2,6-dimethylthiophenoxy, 2,6-diethylthiophenoxy, 2,6-diisopropylthiophenoxy, 2,6-di(2-butyl)thiophenoxy, 2,6-di(n-butyl)thiophenoxy, 2,6-di(2-hexyl)thiophenoxy, 2,6-di(n-hexyl)thiophenoxy, 2,6-di(2-dodecyl)thiophenoxy, 2,6-di(n-dodecyl)thiophenoxy, 2,6-dicyclohexylthiophenoxy, 2,6-dimethyl-4-(n-butyl)thiophenoxy, 2,6-diethyl-4-(n-butyl) thiophenoxy, 2,6-diisopropyl-4-(n-butyl)thiophenoxy, 2,6-di(2-butyl)-4-(n-butyl)-thiophenoxy, 2,4,6-tri-(n-butyl) thiophenoxy, 2,6-di(2-hexyl)-4-(n-butyl)thiophenoxy, 2,6-di(n-hexyl)-4-(n-butyl)thiophenoxy, 2,6-di(2-dodecyl)-4-(n-butyl)thiophenoxy, 2,6-di(n-dodecyl)-4-(n-butyl) thiophenoxy, 2,6-dicyclohexyl-4-(n-butyl)thiophenoxy, 2,6-di-methyl-4-(n-nonyl)thiophenoxy, 2,6-diethyl-4-(n-nonyl) thiophenoxy, 2,6-diisopropyl-4-(n-nonyl)thiophenoxy, 2,6-di(2-butyl)-4-(n-nonyl)thiophenoxy, 2,6-di(2-butyl)-4-(n-nonyl)thiophenoxy, 2,6-di(2-hexyl)-4-(n-nonyl) thiophenoxy, 2,6-di(n-hexyl)-4-(n-nonyl)-thiophenoxy, 2,6-di(2-dodecyl)-4-(n-nonyl)thiophenoxy, 2,6-di(n-dodecyl)-4-(n-nonyl)-thiophenoxy, 2,6-dicyclohexyl-4-(n-nonyl) thiophenoxy, 2,6-(dimethyl)-4-(n-octadecyl)-thiophenoxy, 2,6-(diethyl)-4-(n-octadecyl)thiophenoxy, 2,6-diisopropyl-4-(n-octadecyl)-thiophenoxy, 2,6-di(2-butyl)-4-(n-octadecyl)thiophenoxy, 2,6-di(2-butyl)-4-(n-octadecyl)thiophenoxy, 2,6-di(2-hexyl)-4-(n-octadecyl)thiophenoxy, 2,6-di(n-hexyl)-4-(n-octa-decyl)thiophenoxy, 2,6-di(2-dodecyl)-4-(n-octadecyl)thiophenoxy, 2,6-di(n-dodecyl)-4-(n-octadecyl)thiophenoxy, 2,6-dicyclohexyl-4-(n-octadecyl) thiophenoxy, 2,6-dimethyl-4-(tert-butyl)thiophenoxy, 2,6-diethyl-4-(tert-butyl)thiophenoxy, 2,6-diisopropyl-4-(tert-butyl)thiophenoxy, 2,6-di(2-butyl)-4-(tert-butyl) thiophenoxy, 2,6-di-(n-butyl)-4-(tert-butyl)thiophenoxy, 2,6-di(2-hexyl)-4-(tert-butyl)thiophenoxy, 2,6-di(n-hexyl)-4-(tert-butyl)thiophenoxy, 2,6-di(2-dodecyl)-4-(tert-butyl) thiophenoxy, 2,6-di(n-dodecyl)-4-(tert-butyl)thiophenoxy, 2,6-dicyclohexyl-4-(tert-butyl)thiophenoxy, 2,6-dimethyl-4-(tert-octyl)thiophenoxy, 2,6-diethyl-4-(tert-octyl)thiophenoxy, 2,6-diisopropyl-4-(tert-octyl)thiophenoxy, 2,6-di(2-butyl)-4-(tert-octyl)thiophenoxy, 2,6-di-(n-butyl)-4-(tert-octyl)thiophenoxy, 2,6-di(2-hexyl)-4-(tert-octyl) thiophenoxy, 2,6-di(n-hexyl)-4-(tert-octyl)thiophenoxy, 2,6-di(2-dodecyl)-4-(tert-octyl)thiophenoxy, 2,6-di(n-dodecyl)-4-(tert-octyl)thiophenoxy and 2,6-dicyclohexyl-4-(tert-octyl)thiophenoxy.

In addition, the aromatic skeleton of compounds of the formula (I) may also be substituted by P radicals. These are amino radicals —$NR^1R^2$. The P radicals therefore correspond to (y1) radicals in which L is a chemical bond.

The compounds of the formula (I) may simultaneously be substituted by (het)aryloxy or -thio radicals R and cyclic amino groups P, or either by R radicals or by P radicals. However, they are preferably substituted only by R radicals.

Specific examples of the R, R', R'', R''', $R^{IV}$, $R^{VII}$, $R^{1'}$, $R^{3'}$, $R^{8'}$, and $R^1$ to $R^{10}$ radicals occurring in the compounds of the general formula (I) and their substituents include:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxanonyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetra-oxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl; methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl) dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl) aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl) aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl; phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The use of the compounds of the general formula (I) as active materials in solar cells and photodetectors includes, for example, their use, if appropriate with addition of dopants, as charge transport materials in organic solar cells. In this case, the compounds of the formula (I) typically function as electron transport materials, but they may also act as hole transport materials in the individual case.

In addition, their use as active materials in photodetectors or solar cells also includes, for example, their use as photosensitizers in the DSSCs addressed at the outset.

In addition, their use as active materials in solar cells or photodetectors also includes, for example, their use as a constituent of photoactive layers in organic solar cells, especially also in the bulk heterojunctions addressed at the outset.

In general, for use as photosensitizers in DSSCs, preference is given to using compounds of the formula (I) in which both X are either each a CWWM radical or together are a radical of the formula (x1) where W' is defined as oxygen or sulfur, a radical of the formula (x2) or a radical of the formula (x3), and one Y is either a radical of the formula (y1) or (y2) and the other Y is a hydrogen, or else both Y together are either a (y3) where W' is defined as oxygen or sulfur or a (y4) radical.

In particular, compounds of the formula (I) in which both X are either each a CWWM radical or together are a radical of the formula (x1) where W' is defined as oxygen or sulfur, a radical of the formula (x2) or a radical of the formula (x3), and one Y is a radical of the formula (y1) or (y2) and the other Y is a hydrogen, are typically used as sensitizers.

In general, for use in organic solar cells, preference is given to using compounds of the formula (I) in which both X together are a radical of the formula (x1) where W' is defined as oxygen or sulfur, a radical of the formula (x2) or a radical of the formula (x3), and both Y together are either a (y3) radical where W is defined as oxygen, sulfur or N—R', or a (y4) radical.

When the compounds of the general formula (I), both in their use in DSSCs and in organic solar cells, are to be processed in liquid form, it is advantageous, as already addressed above, to insert substituents into the aromatic skeleton.

The present invention accordingly further provides for the use of mixtures comprising, as components, K1) compounds of the general formula (I) and their preferred embodiments as electron donors or electron acceptors and
K2) one or more compounds which, with respect to component K1, act correspondingly as electron acceptors or electron donors for producing photoactive layers for solar cells or photodetectors.

Preferred use in accordance with the invention is found by mixtures wherein component K1 is present in a proportion of from 30 to 70% by mass and component K2 in a proportion of from 70 to 30% by mass, where the proportions of components K1 and K2, based in each case on the total mass of components K1 and K2, add up to 100% by mass.

Particularly preferred use in accordance with the invention is found by mixtures wherein component K1 is present in a proportion of from 40 to 60% by mass and component K2 in a proportion of from 60 to 40% by mass, where the proportions of components K1 and K2, based in each case on the total mass of components K1 and K2, add up to 100% by mass.

Organic solar cells usually have a layered structure and generally comprise at least the following layers: electrode, photoactive layer and counterelectrode. These layers are generally disposed on a substrate customary therefor. Suitable substrates are, for example, oxidic materials, for instance glass, quartz, ceramic, $SiO_2$, etc., polymers, for instance polyvinyl chloride, polyolefins, e.g. polyethylene and polypropylene, polyesters, fluoropolymere, polyamides, polyurethanes, polyalkyl (meth)acrylates, polystyrene and mixtures and composites thereof, and combinations of the substrates listed above.

Suitable materials for one electrode are especially metals, for example the alkali metals Li, Na, K, Rb and Cs, the alkaline earth metals Mg, Ca and Ba, Pt, Au, Ag, Cu, Al, In, metal alloys, for example based on Pt, Au, Ag, Cu, etc., and specific Mg/Ag alloys, but additionally also alkali metal fluorides, such as LiF, NaF, KF, RbF and CsF, and mixtures of alkali metal fluorides and alkali metals. The electrode used is preferably a material which essentially reflects the incident light. These include, for example, metal films of Al, Ag, Au, In, Mg, Mg/Al, Ca, etc.

The counterelectrode consists of a material essentially transparent to incident light, for example ITO, doped ITO, FTO, ZnO, $TiO_2$, Cu, Ag, Au and Pt, the latter metals being present in correspondingly thin layers.

"Transparent" shall be understood here to mean an electrode/counterelectrode when at least 50% of the radiation intensity in the wavelength range in which the photoactive layer absorbs radiation is transmitted. In the case of a plurality of photoactive layers, an electrode/counterelectrode shall be considered to be "transparent" when at least 50% of the radiation intensity in the wavelength range in which the photoactive layers absorb radiation is transmitted.

In the photoactive layers, component K1 may assume the role of electron donor; accordingly, component K2 then takes on the role of electron acceptor. Alternatively, however, component K1 may also assume the role of electron acceptor; accordingly, component K2 then functions as an electron donor. The manner in which the particular component acts depends on the energy of the HOMO or LUMO of component K1 in relation to the energy of the HOMO or LUMO of component K2. The compounds of component K1 typically appear as electron acceptors. In particular, this is to be expected when the components K2 used are merocyanines of the D-A structure, as described in prior European patent application 07 112 153.7, and in which D is a donor unit and A is an acceptor unit in the molecule. In general, the merocyanines then act as electron donors. These roles may, however, be exchanged in the specific individual case. It should also be noted that component K2 may likewise obey the structural definition of component K1, such that a compound of the general formula (I) may assume the role of an electron donor, and another compound of the general formula (I) the role of an electron acceptor.

In addition, component K2 may, for example, also comprise the phthalocyanines described at the outset, for example zinc phthalocyanine or vanadyl phthalocyanine, or polymers, for example poly(3-hexylthiophene) ("P3HT"), poly(2-methoxy—S—(3,7-dimethyloctyloxy)-1,4-phenylenevinylene) ("$OC_1C_{10}$-PPV"). Compared to these compounds, the compounds of the formula (I) as component K1 typically likewise act as electron acceptors.

In addition to the photoactive layer, it is possible for one or more further layers to be present in the inventive organic solar cells and photodetectors, for example electron transporting layers ("ETLs") and/or hole transporting layers ("HTLs") and/or blocking layers, e.g. exciton blocking layers ("EBLs") which typically do not absorb the incident light, or else layers which serve as charge transport layers and simultaneously improve the contacting to one or both electrodes of the solar cell. The ETLs and HTLs may also be doped, so as to give rise to cells of the p-i-n type, as described, for example, in the publication by J. Drechsel et al., Thin Solid Films 451-452 (2004), 515-517.

The construction of organic solar cells is additionally described, for example, in the documents WO 2004/083958 A2, US 2005/0098726 A1 and US 2005/0224905 A1, which are hereby fully incorporated by reference.

Photodetectors essentially have a structure analogous to organic solar cells, but are operated with suitable bias voltage which generates a corresponding current flow as a measurement response under the action of radiative energy.

The photoactive layers are processed, for example, from solution. In this case, components K1 and K2 may already be dissolved together, but may also be present separately as a solution of component K1 and a solution of component K2, in which case the corresponding solutions are mixed just before application to the layer below. The concentrations of components K1 and K2 generally vary from a few g/l to a few tens of g/l of solvent.

Suitable solvents are all liquids which evaporate without residue and have a sufficient solubility for components K1 and K2. Useful examples include aromatic compounds, for example benzene, toluene, xylene, mesitylene, chlorobenzene or dichlorobenzene, trialkylamines, nitrogen-containing heterocycles, N,N-disubstituted aliphatic carboxamides, for instance dimethylformamide, diethylformamide, dimethylacetamide or dimethylbutyramide, N-alkyllactams, for instance N-methylpyrrolidone, linear and cyclic ketones, for instance methyl ethyl ketone, cyclopentanone or cyclohexanone, cyclic ethers, for instance tetrahydrofuran, or alcohols, for instance methanol, ethanol, propanol, isopropanol or butanol.

In addition, it is also possible for mixtures of the aforementioned solvents to find use.

Suitable methods for applying the inventive photoactive layers from the liquid phase are known to those skilled in the art. What is found to be advantageous here is especially processing by means of spin-coating, since the thickness of the photoactive layer can be controlled in a simple manner by the amount and/or concentration of the solution used, and also the rotation speed and/or rotation time. The solution is generally processed at room temperature.

Moreover, in the case of suitable selection of components K1 and K2, processing from the gas phase is also possible, especially by vacuum sublimation. The present invention further provides for the use of compounds of the general formula (I) and of their preferred embodiments as photosensitizers in solar cells or photodetectors.

The present invention further provides solar cells and photodetectors comprising compounds of the general formula (I) and their preferred embodiments or mixtures comprising the components K1 and K2 detailed above.

The present invention further provides compounds of the general formula (I) and their preferred embodiments detailed above in the context of their inventive use.

Particular preference is given here to inventive compounds of the formula (I) wherein the variables are each defined as follows:

X are joined together with formation of a six-membered ring to give a radical of the formula (x1), or both are each a —CWWM radical;

Y one of the two radicals is a radical of the formula (y1) or (y2) and the other radical is hydrogen, or they are joined to one another with formation of a six-membered ring to give a radical of the formula (y3);

R are identical or different radicals:
  phenoxy or thiophenoxy, each of which may be mono- or polysubstituted by identical or different (i), (ii), (iii), (iv) and/or (v) radicals:
  (i) $C_1$-$C_{30}$-alkyl whose carbon chain may be interrupted by one or more nonadjacent —O—, —S—, —NR$^4$—, —C≡C—, —CR$^4$=CR$^4$— and/or —CO— and/or —SO$_2$— moieties and which may be mono- or polysubstituted by: $C_1$-$C_{12}$-alkoxy, hydroxyl, halogen, cyano and/or aryl which may be mono- or polysubstituted by $C_1$-$C_{18}$-alkyl or $C_1$-$C_6$-alkoxy;
  (ii) $C_3$-$C_8$-cycloalkyl whose carbon skeleton may be interrupted by one or more nonadjacent —O—, —S—, —NR$^4$—, —CR$^4$=CR$^4$— and/or —CO— moieties and which may be mono- or polysubstituted by $C_1$-$C_{18}$-alkyl, $C_1$-$C_{12}$-alkoxy and/or $C_1$-$C_6$-alkylthio;
  (iii) aryl or hetaryl, to each of which may be fused further 5- to 7-membered saturated or unsaturated rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by: $C_1$-$C_{18}$-alkyl, $C_1$-$C_{12}$-alkoxy, —C=CR$^4$$_2$, —CR$^4$=CR$^4$$_2$, hydroxyl, halogen, cyano, —NR$^9$R$^{10}$, —NR$^5$COR$^6$, —CONR$^5$R$^6$, —SO$_2$NR$^5$R$^6$, —COOR$^7$, —SO$_3$R$^7$, (het)aryl, (het)aryloxy and/or (het)arylthio, where the (het)aryl radicals may each be mono- or polysubstituted by $C_1$-$C_{18}$-alkyl, $C_1$-$C_{18}$-alkoxy and/or cyano;
  (iv) a —U-aryl radical which may be mono- or polysubstituted by the above radicals mentioned as substituents for the aryl radicals (iii), where U is an —O—, —S—, —NR$^4$—, —CO—, —SO— or —SO$_2$— moiety;
  (v) $C_1$-$C_{12}$-alkoxy, $C_1$-$C_6$-alkylthio, —C=CR$^4$, —CR$^4$=CR$^4$$_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$ and/or —SO$_3$R$^7$;

M is hydrogen, an alkali metal cation or [NR$^5$]$_4$$^+$;

L is a chemical bond or phenylene;

R$^1$, R$^2$ are identical or different phenyl radicals which may each be mono- or polysubstituted by $C_1$-$C_{18}$-alkyl, $C_1$-$C_{12}$-alkoxy, $C_1$-$C_6$-alkyl-thio, —NR$^5$R$^6$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio and/or —NR$^5$R$^6$; joined to the nitrogen atom to form a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by: $C_1$-$C_{24}$-alkyl which may be substituted by $C_1$-$C_{18}$-alkoxy, $C_1$-$C_{18}$-alkylthio and/or —NR$^5$R$^6$, (het)aryl which may be mono- or polysubstituted by $C_1$-$C_{18}$-alkyl and/or the above radicals mentioned as substituents for alkyl, $C_1$-$C_{18}$-alkoxy, $C_1$-$C_{18}$-alkylthio and/or —NR$^5$R$^6$;

Z is —O— or —S—;

R$^3$ is $C_1$-$C_{30}$-alkyl whose carbon chain may be interrupted by one or more nonadjacent —O—, —S— and/or —NR$^4$- moieties and which may be mono- or polysubstituted by: $C_1$-$C_{12}$-alkoxy, hydroxyl and/or aryl which may be mono- or polysubstituted by $C_1$-$C_{18}$-alkyl or $C_1$-$C_6$-alkoxy;
  phenyl which may be mono- or polysubstituted by: $C_1$-$C_{18}$-alkyl, $C_1$-$C_{12}$-alkoxy, $C_1$-$C_6$-alkylthio, —NR$^5$R$^6$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio and/or —NR$^5$R$^6$;

R' is $C_6$-$C_{30}$-alkyl whose carbon chain may be interrupted by one or more nonadjacent —O—, —S— and/or —NR$^4$- moieties and which may be mono- or polysubstituted by: $C_1$-$C_6$-alkoxy, $C_1$-$C_6$-alkylthio, —NR$^9$R$^{10}$ and/or aryl which may be mono- or polysubstituted by $C_1$-$C_{18}$-alkyl or $C_1$-$C_6$-alkoxy;
  phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —NR$^9$R$^{10}$, —CONR$^5$R$^6$, —SO$_2$NR$^5$R$^6$ and/or phenoxy, phenylthio, phenylazo and/or naphthylazo, each of which may be substituted by $C_1$-$C_{10}$-alkyl, $C_1$-$C_6$-alkoxy and/or cyano;

R$^4$ is hydrogen or $C_1$-$C_6$-alkyl;

R$^5$, R$^6$ are each independently:
  hydrogen;
  $C_1$-$C_{18}$-alkyl which may be mono- or polysubstituted by $C_1$-$C_6$-alkoxy, hydroxyl, halogen and/or cyano;
  aryl or hetaryl, each of which may be mono- or polysubstituted by $C_1$-$C_6$-alkyl and/or the above radicals mentioned as substituents for alkyl,
  where the R$^5$ radicals may be the same or different when they occur more than once;

R$^7$ is $C_1$-$C_{18}$-alkyl which may be mono- or polysubstituted by $C_1$-$C_6$-alkoxy, hydroxyl, halogen and/or cyano;
  aryl or hetaryl, each of which may be mono- or polysubstituted by $C_1$-$C_6$-alkyl and/or the above radicals mentioned as substituents for alkyl;

R$^9$, R$^{10}$ are each independently $C_1$-$C_{30}$-alkyl whose carbon chain may be interrupted by one or more nonadjacent —O—, —S—, —NR$^4$—, —N=CR$^4$—, —C≡C— and/or —CR$^4$=CR$^4$— moieties and which may be mono- or polysubstituted by: $C_1$-$C_{12}$-alkoxy, $C_1$-$C_6$-alkylthio, —C=CR$^4$, —CR$^4$=CR$^4$$_2$, hydroxyl, —NR$^5$R$^6$, —NR$^5$COR$^6$ and/or (het)aryl which may be mono- or polysubstituted by $C_1$-$C_{18}$-alkyl and/or the above radicals mentioned as substituents for alkyl;
  aryl or hetaryl, to which may be fused further saturated or unsaturated 5- to 7-membered rings whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C=CR$^4$, —CR$^4$=CR$^4$$_2$, hydroxyl, —NR$^5$R$^6$, —NR$^5$COR$^6$, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, hydroxyl, —NR$^5$R$^6$ and/or —NR$^5$COR$^6$;

joined to the nitrogen atom to form a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by $C_1$-$C_{24}$-alkyl which may be substituted by $C_1$-$C_{18}$-alkoxy, $C_1$-$C_{18}$-alkylthio and/or —$NR^5R^6$;

m is 2, 3 or 4;

n is 4 when m=2 or 3;

is 4 or 6 when m=4;

p is 0.

The present invention further provides mixtures comprising, as components,

K1) compounds of the general formula (I) and their preferred embodiments as electron donors or electron acceptors and K2) one or more compounds which, with respect to component K1, act correspondingly as electron acceptors or electron donors.

Possible compounds as component K2 have already been addressed above.

In particular, the inventive mixtures find use in the form of a bicontinuous phase ("bulk heterojunction") in photoactive layers of organic solar cells.

EXAMPLES

I. Preparation of the Compounds of the General Formula (I)

Example 1

A 50 ml two-neck flask with a stirrer bar, condenser and nitrogen attachment was, while purging with nitrogen, initially charged with 300 mg (0.28 mmol) of the compound

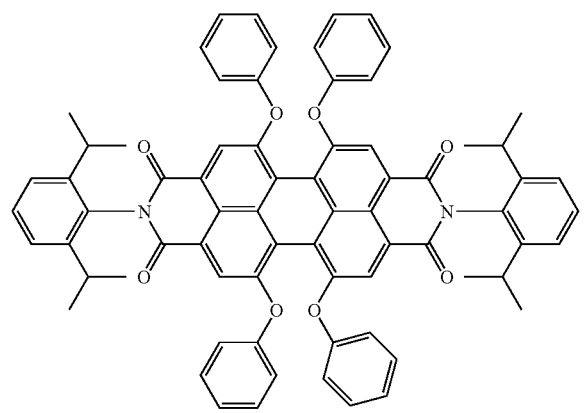

(Lumogen® F Rot 300, BASF Aktiengesellschaft) in 40 ml of anhydrous toluene, which were admixed with 160 mg (0.56 mmol) of the compound

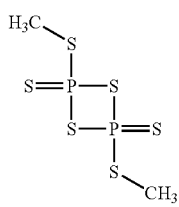

(Davy reagent). After heating to reflux, the mixture was stirred under reflux overnight. After the mixture had been cooled, it was possible by thin layer chromatography (eluent: toluene) to detect a little monosulfated compound

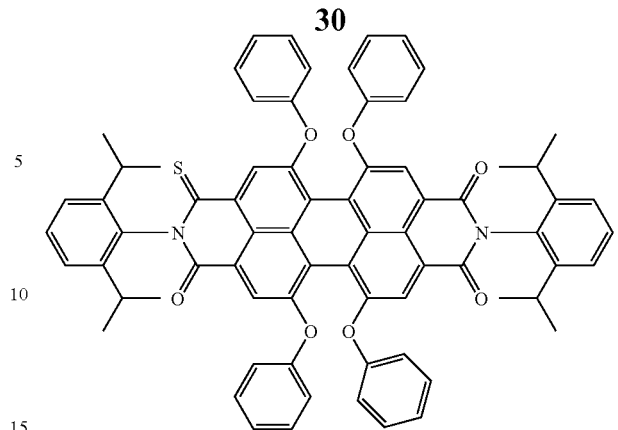

a lot of the disulfated compounds as a mixture of the isomers

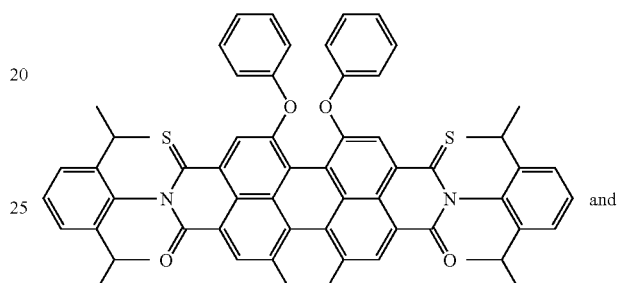

and

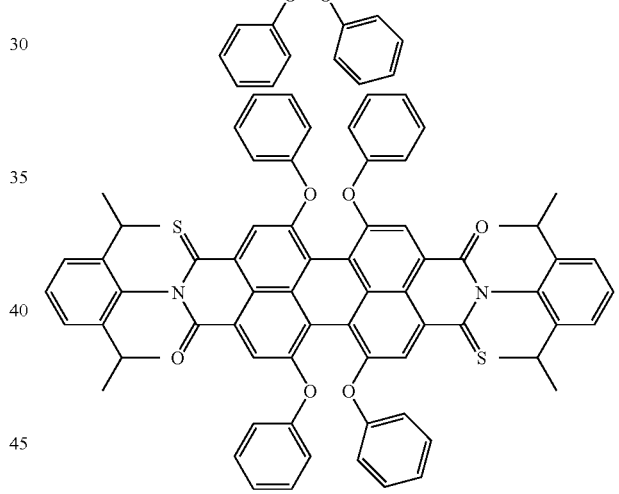

and the isomer

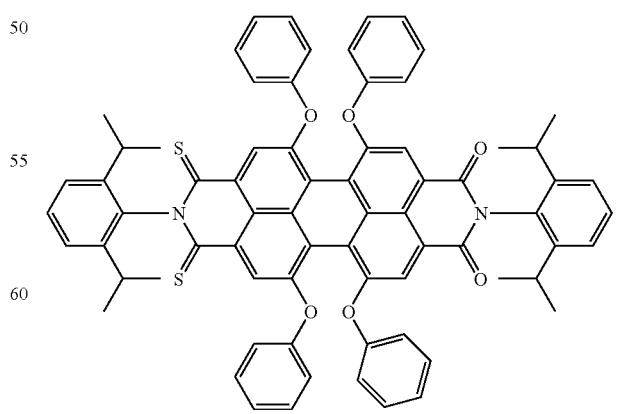

might possibly also have been present, but was not analyzed in detail, and a little of the trisulfated compound

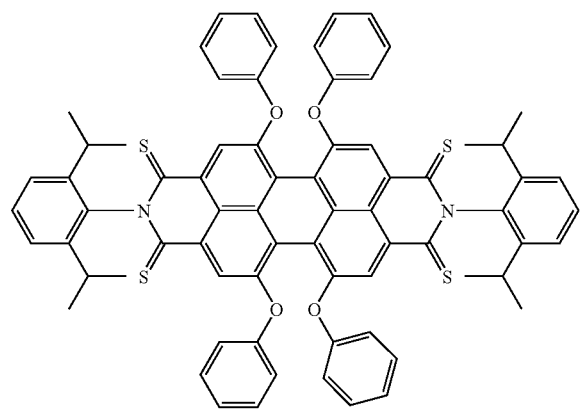

Another 160 mg (0.56 mmol) of Davy reagent were added, the mixture was heated to reflux and the mixture was kept under reflux for a duration of 1.5 days. After the mixture had been cooled, it was possible by thin-layer chromatography to detect traces of the tetrasulfated compound

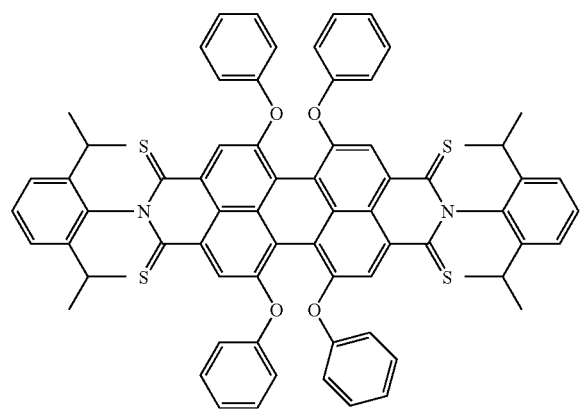

The mass spectroscopy data and absorbance maxima of the mono-, di-, tri- and tetrasulfate compound are listed below:
Mono: MS (FD): m/z (rel. int.)=1094.4 (100%) [M⁺]
    UV-Vis (CHCl₃):=610 nm;
MS (FD): m/z (rel. int.)=1111.3 (100%) [M⁺]
    UV-Vis (CHCl₃):=649 nm;
Tri: MS (FD): m/z (rel. int.)=1127.2 (100%) [M⁺]
    UV-Vis (CHCl₃):=701 nm;
Tetra: MS (FD): m/z (rel. int.)=1143.3 (100%) [M⁺]
    UV-Vis (CHCl₃):=750 nm.

The starting compound exhibited an absorbance maximum at 567 nm.

With increasing degree of sulfation, the wavelength of the absorbance maximum increases; it is therefore possible through the degree of sulfation to exactly adjust the absorption behavior of the compounds of the formula (I) to the particular requirements.

Experiments Using the Lawesson Reagent

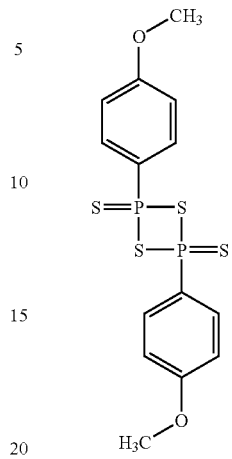

afforded the same result as those with the Davy reagent.

Example 2

A 50 ml two-neck flask with a stirrer bar, condenser and nitrogen attachment was, while purging with nitrogen, initially charged with 50 mg (0.03 mmol) of the compound

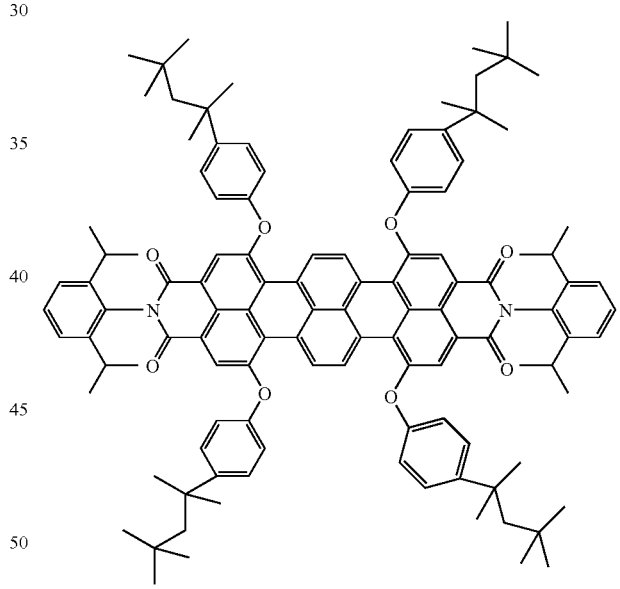

in 10 ml of anhydrous toluene, which were admixed in portions with 220 mg (0.54 mmol) of the Lawesson reagent and heated at reflux over 60 hours. After the mixture had been cooled, it was possible by thin-layer chromatography (eluent: toluene) to detect all sulfated (mono, di, tri, tetra) compounds. The di- and trisulfated compound were isolated.

The mass spectroscopy data and absorbance maxima of the mono-, di and trisulfated compound are listed below:
Start: UV-Vis (CHCl₃):=676 nm;
Di: MS (FD): m/z (rel. int.)=1683.0 (100%) [M⁺]
    UV-Vis (CHCl₃):=765 nm;
MS (FD): m/z (rel. int.)=1699.1 (100%) [M⁺]
    UV-Vis (CHCl₃):=820 nm.

With increasing degree of sulfation, the wavelength of the absorbance maximum likewise increases significantly.

Example 3

A 50 ml two-neck flask with a stirrer bar, condenser and nitrogen attachment was, while purging with nitrogen, initially charged with 400 mg (0.23 mmol) of the compound

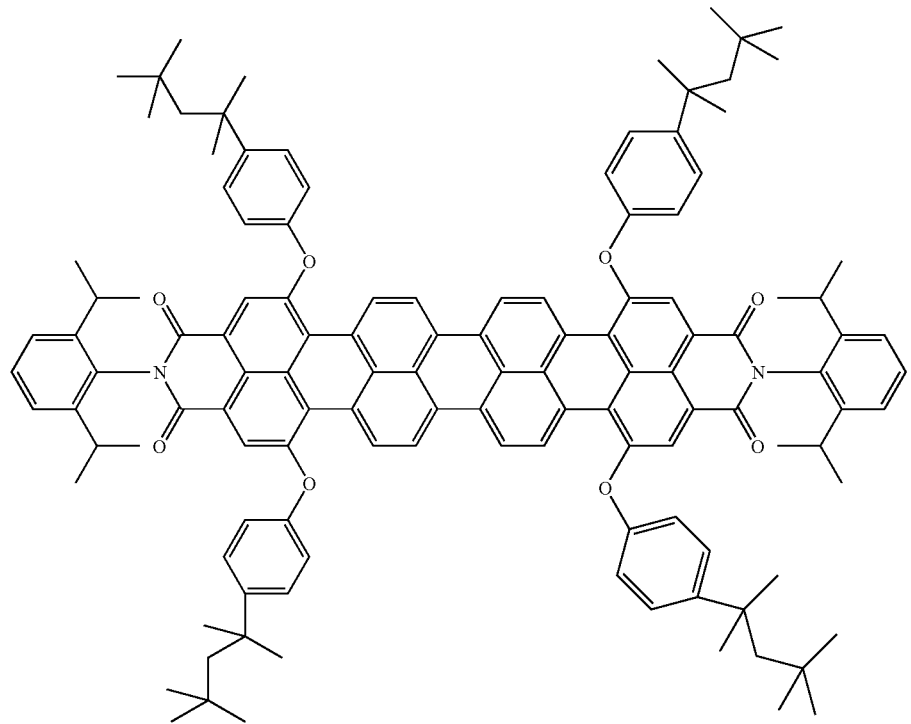

in 20 ml of anhydrous toluene, which were admixed in portions with a total of 1.5 g (3.6 mmol) of the Lawesson reagent and heated at reflux over 72 hours. After the mixture had been cooled, it was possible by thin-layer chromatography (eluent: toluene) to detect all sulfated (mono, di, tri, tetra) compounds. The di-, tri- and tetrasulfated compound were detected.

The mass spectroscopy data and absorbance maxima of the di-, tri- and tetrasulfated compound are listed below:

Start: UV-Vis $(CHCl_3)$:=780 nm;

Di: MS (FD): m/z (rel. int.)=1806.9 (100%) $[M^+]$
UV-Vis $(CHCl_3)$:=874 nm;

Tri: MS (FD): m/z (rel. int.)=1822.8 (100%) $[M^+]$
UV-Vis $(CHCl_3)$:=917 nm;

Tetra: MS (FD): m/z (rel. int.)=1838.9 (100%) $[M^+]$
UV-Vis $(CHCl_3)$:=955 nm.

With increasing degree of sulfation, the wavelength of the absorbance maximum likewise increases significantly.

Example 4

A 50 ml two-neck flask with a stirrer bar, condenser and nitrogen attachment was initially charged, while purging with nitrogen, with 300 mg (0.4 mmol) of the compound

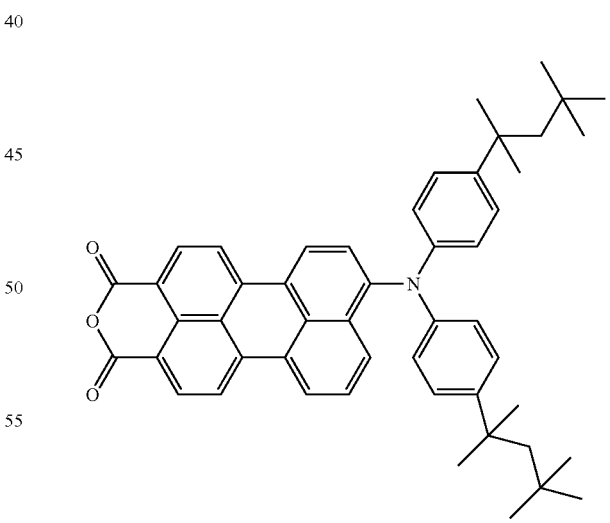

in 10 ml of anhydrous toluene, which were admixed in portions with a total of 340 mg (0.8 mmol) of the Lawesson reagent) and heated at reflux over 3 hours. After the mixture had been cooled, it was possible by thin-layer chromatography (eluent: dichloromethane) to isolate 130 mg (yield: 44% of theory) of the disulfated compound in the form of a green solid.

The mass spectroscopy and IR spectroscopy data and the absorbance maximum of the disulfated compound are listed below:
Start: UV-Vis (CH$_2$Cl$_2$):=608 nm;
MS (FD): m/z (rel. int.)=745.3 (100%) [M$^+$]
UV-Vis (CHCl$_3$):=734 nm.

Example 5

A 50 ml two-neck flask with a stirrer bar, condenser and nitrogen attachment was, while purging with nitrogen, initially charged with 240 mg (0.34 mmol) of the compound

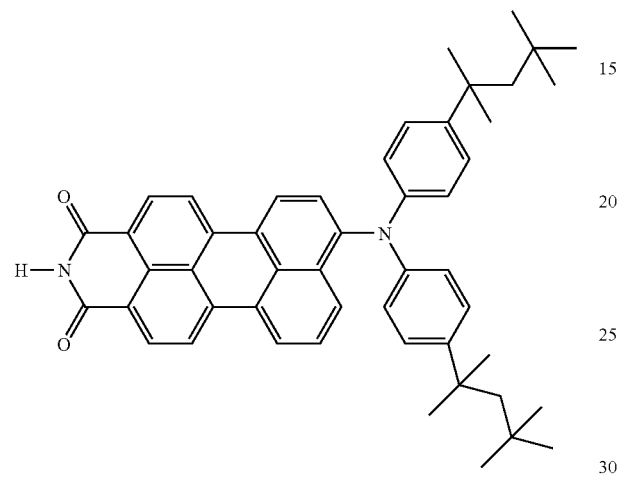

in 10 ml of anhydrous toluene, which were admixed in portions with a total of 550 mg (1.36 mmol) of the Lawesson reagent and heated at reflux over 5 hours. After the mixture had been cooled, it was possible by thin-layer chromatography (eluent: 1:1 dichloromethane/hexane) to isolate the disulfated compound.
The mass spectroscopy data and the absorbance maximum of the disulfated compound are listed below:
Start: UV-Vis (CH$_2$Cl$_2$):=588 nm;
Di: MS (FD): m/z (rel. int.)=744.4 (100%) [M$^+$]
UV-Vis (CHCl$_3$):=734 nm.

Example 6

A 50 ml two-neck flask with a stirrer bar, condenser and nitrogen attachment was, while purging with nitrogen, initially charged with 200 mg (0.14 mmol) of the compound

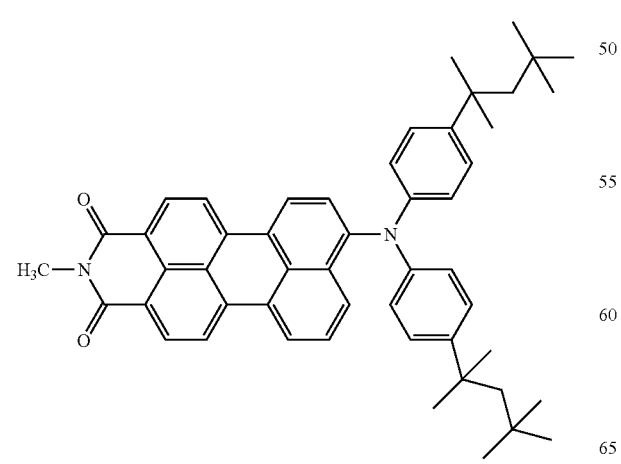

in 10 ml of anhydrous toluene, which were admixed in portions with a total of 680 mg (1.684 mmol) of the Lawesson reagent and heated at reflux over 24 hours. After the mixture had been cooled, it was possible by thin-layer chromatography (eluent: dicchloromethane/hexane 1:1) to isolate the disulfated compound.
The mass spectroscopy data and the absorbance maximum of the disulfated compound are listed below:
Start: UV-Vis (CH$_2$Cl$_2$):=578 nm;
Di: MS (FD): m/z (rel. int.)=758.3 (100%) [M$^+$]
UV-Vis (CHCl$_3$):=714 nm.

Example 7

A 50 ml two-neck flask with a stirrer bar, condenser and nitrogen attachment was, while purging with nitrogen, initially charged with 300 mg (0.4 mmol) of the compound

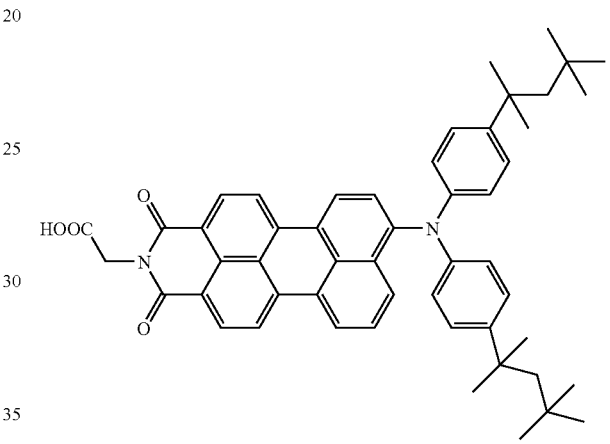

in 20 ml of anhydrous toluene, which were admixed in portions with a total of 220 mg (0.8 mmol) of the Davy reagent and heated at reflux over 18 hours. After the mixture had been cooled and the solvent drawn off, it was possible to isolate the monosulfated compound.
The mass spectroscopy data and the absorbance maximum of the monosulfated compound are listed below:
Start: UV-Vis (CH$_2$Cl$_2$):=568 nm;
Mono: MS (FD): m/z (rel. int.)=784.4 (100%) [M$^+$]
UV-Vis (CHCl$_3$):=591 nm.

The invention claimed is:

1. An active material in solar cells or photodetectors comprising a compound of the general formula (I)

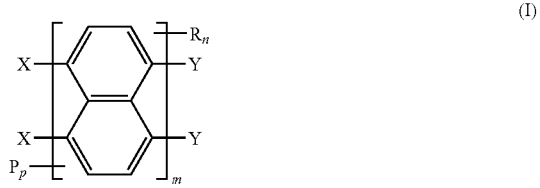

in which the variables are each defined as follows:
X are joined to one another with formation of a six-membered ring to give a radical of the formula (x1), (x2) or (x3)

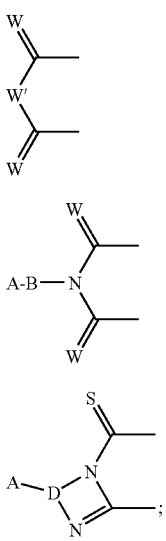

(x1)

(x2)

(x3)

or both are each a —CWWM radical;
Y one of the two radicals is either a radical of the formula (y1)

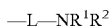 (y1)

or a radical of the formula (y2)

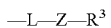 (y2)

and the other radical is hydrogen;
or are joined to one another with formation of a six-membered ring to give a radical of the formula (y3) or (y4)

(y3)

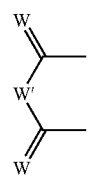 (y4)

;

or both are hydrogen;
W are each independently O or S;
W' is O, S or N—R',
  with the proviso that at least one of the variables W or W' in the general formula I is defined as S;
R are identical or different radicals:
  aryloxy, arylthio, hetaryloxy or hetarylthio, to each of which may be fused further saturated or unsaturated 5- to 7-membered rings whose carbon skeleton may be interrupted by one or more nonadjacent —O—, —S—, —NR$^4$—, —N═CR$^4$—, —CO—, —SO— and/or —SO$_2$— moieties, where the entire ring system may be mono- or polysubstituted by the following (i), (ii), (iii), (iv) and/or (v) radicals:
  (i) C$_1$-C$_{30}$-alkyl whose carbon chain may be interrupted by one or more nonadjacent —O—, —S—, —NR$^4$—, —N═CR$^4$—, —C≡C—, —CR$^4$═CR$^4$—, —CO—, —SO— and/or —SO$_2$— moieties and which may be mono- or polysubstituted by: C$_1$-C$_{12}$-alkoxy, C$_1$-C$_6$-alkylthio, —C≡CR$^4$, —CR$^4$═CR$^4$$_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7$$_2$, —POR$^7$R$^7$, (het)aryl and/or saturated or unsaturated C$_4$-C$_7$-cycloalkyl whose carbon skeleton may be interrupted by one or more nonadjacent —O—, —S—, —NR$^4$—, —N═CR$^4$—, —CR$^4$═CR$^4$—, —CO—, —SO— and/or —SO$_2$— moieties, where the (het)aryl and cycloalkyl radicals may each be mono- or polysubstituted by C$_1$-C$_{18}$-alkyl and/or the above radicals mentioned as substituents for alkyl;
  (ii) C$_3$-C$_8$-cycloalkyl whose carbon skeleton may be interrupted by one or more nonadjacent —O—, —S—, —NR$^4$—, —N═CR$^4$—, —CR$^4$═CR$^4$—, —CO—, —SO— and/or —SO$_2$— moieties and to which may be fused further saturated or unsaturated 5- to 7-membered rings whose carbon skeleton may be interrupted by one or more nonadjacent —O—, —S—, —NR$^4$—, —N═CR$^4$—, —CR$^4$═CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$═CR$^4$$_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7$$_2$ and/or —POR$^7$R$^7$;
  (iii) aryl or hetaryl, to which may be fused further saturated or unsaturated 5-7-membered rings whose carbon skeleton may be interrupted by one or more nonadjacent —O—, —S—, —NR$^4$—, —N═CR$^4$—, —CR$^4$═CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$═CR$^4$$_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7$$_2$, —POR$^7$R$^7$, (het)aryl, (het)aryloxy and/or (het)arylthio, where the (het)aryl radicals may each be mono- or polysubstituted by C$_1$-C$_{18}$-alkyl, C$_1$-C$_{12}$-alkoxy, C$_1$-C$_6$-alkylthio, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7$$_2$, —POR$^7$R$^7$;
  (iv) a —U-aryl radical which may be mono- or polysubstituted by the above radicals mentioned as substituents for the aryl radicals (iii), where U is an —O—, —S—, —NR$^4$—, —CO—, —SO— or —SO$_2$— moiety; and
  (v) C$_1$-C$_{12}$-alkoxy, C$_1$-C$_6$-alkylthio, —C≡CR$^4$, —CR$^4$═CR$^4$$_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7$$_2$ and/or —POR$^7$R$^7$;
P is an amino radical —NR$^1$R$^2$;
B is C$_1$-C$_6$-alkylene, phenylene or combinations of these bridging members, where the phenylene radicals may be mono- or polysubstituted by C$_1$-C$_{12}$-alkyl, nitro, cyano and/or halogen;
A is —COOM, —SO$_3$M or —PO$_3$M$_2$;
D is 1,2-phenylene, 1,2- or 2,3-naphthylene or 2,3- or 3,4-pyridylene, each of which may be mono- or polysubstituted by C$_1$-C$_{12}$-alkyl, C$_1$-C$_{12}$-alkoxy, hydroxyl, nitro and/or halogen;
M is hydrogen, an alkali metal cation or [NR$^5$]$_4$$^+$;
L is a chemical bond or an arylene or hetarylene radical which is bonded to the rylene skeleton directly or via ethenylene or ethynylene and is of the formulae —Ar—  —Ar-E-Ar— in which the (het)arylene radicals Ar may be the same or different, may comprise heteroatoms as ring atoms and/or may comprise fused saturated or unsaturated 5- to 7-membered rings which may likewise comprise heteroatoms, where the entire ring system may be mono- or polysubstituted by phenyl, $C_1$-$C_{12}$-alkyl, $C_1$-$C_{12}$-alkoxy, $C_1$-$C_{12}$-alkylthio and/or —$NR^5R^6$;

E is a chemical bond or an —O—, —S—, —$NR^4$—, —C≡C—, —$CR^4$=$CR^4$— or $C_1$-$C_6$-alkylene moiety;

$R^1$, $R^2$ are each independently one of the alkyl radicals (i), cycloalkyl radicals (ii) or (het)aryl radicals (iii) mentioned as substituents for the R radicals;

joined to one another to form a saturated or unsaturated, 5- to 7-membered ring which comprises the nitrogen atom and whose carbon chain may be interrupted by one or more nonadjacent —O—, —S— and/or —$NR^4$-moieties, to which may be fused one or two unsaturated or saturated 4- to 8-membered rings whose carbon chain may likewise be interrupted by these nonadjacent moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the above radicals mentioned as substituents for alkyl, $C_1$-$C_{18}$-alkoxy, $C_1$-$C_{18}$-alkylthio and/or —$NR^5R^6$;

Z is —O— or —S—;

$R^3$ is one of the alkyl radicals (i) or (het)aryl radicals (iii) mentioned as substituents for the R radicals;

R' is hydrogen;

$C_1$-$C_{30}$-alkyl whose carbon chain may be interrupted by one or more nonadjacent —O—, —S—, —$N$=$CR^4$—, —C≡C—, —$CR^4$=$CR^4$—, —CO—, —SO— and/or —$SO_2$— moieties and which may be mono- or polysubstituted by the (ii), (iii), (iv) and/or (v) radicals mentioned as substituents for the R radicals;

$C_3$-$C_8$-cycloalkyl to which may be fused further saturated or unsaturated 5- to 7-membered rings whose carbon skeleton may be interrupted by one or more nonadjacent —O—, —S—, —$NR^4$—, —$N$=$CR^4$—, —$CR^4$=$CR^4$—, —CO—, —SO— and/or —$SO_2$— moieties, where the entire ring system may be mono- or polysubstituted by the (i), (ii), (iii), (iv) and/or (v) radicals mentioned as substituents for the R radicals;

aryl or hetaryl, to which may be fused further saturated or unsaturated 5- to 7-membered rings whose carbon skeleton may be interrupted by one or more nonadjacent —O—, —S—, —$NR^4$—, —$N$=$CR^4$—, —$CR^4$=$CR^4$—, —CO—, —SO— and/or —$SO_2$— moieties, where the entire ring system may be mono- or polysubstituted by the (i), (ii), (iii), (iv), (v) radicals mentioned as substituents for the R radicals, and/or aryl- and/or hetarylazo which may each be substituted by $C_1$-$C_{10}$-alkyl, $C_1$-$C_6$-alkoxy and/or cyano;

$R^4$ is hydrogen or $C_1$-$C_{18}$-alkyl, where the $R^4$ radicals may be the same or different when they occur more than once;

$R^5$, $R^6$ are each independently:

hydrogen;

$C_1$-$C_{18}$-alkyl whose carbon chain may be interrupted by one or more nonadjacent —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^8$;

aryl or hetaryl, to each of which may be fused further saturated or unsaturated 5- to 7-membered rings whose carbon skeleton may be interrupted by one or more nonadjacent —O—, —S—, —CO— and/or —$SO_2$— moieties, where the entire ring system may be mono- or polysubstituted by $C_1$-$C_{12}$-alkyl and/or the above radicals mentioned as substituents for alkyl, where the $R^5$ radicals may be the same or different when they occur more than once;

$R^7$ is $C_1$-$C_{18}$-alkyl whose carbon chain may be interrupted by one or more nonadjacent —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^8$;

aryl or hetaryl, to each of which may be fused further saturated or unsaturated 5- to 7-membered rings whose carbon skeleton may be interrupted by one or more nonadjacent —O—, —S—, —CO— and/or —$SO_2$— moieties, where the entire ring system may be mono- or polysubstituted by $C_1$-$C_{12}$-alkyl and/or the above radicals mentioned as substituents for alkyl, where the $R^7$ radicals may be the same or different when they occur more than once;

$R^8$ is $C_1$-$C_{18}$-alkyl;

$R^9$, $R^{10}$ are each independently $C_1$-$C_{30}$-alkyl whose carbon chain may be interrupted by one or more nonadjacent —O—, —S—, —$NR^4$—, —$N$=$CR^4$—, —C≡—, —$CR^4$=$CR^4$—, —CO—, —SO— and/or —$SO_2$— moieties and which may be mono- or polysubstituted by: $C_1$-$C_{12}$-alkoxy, $C_1$-$C_6$-alkylthio, —C≡$CR^4$, —$CR^4$=$CR^4{}_2$, hydroxyl, —$NR^5R^6$, —$NR^5COR^6$, (het)aryl and/or saturated or unsaturated $C_4$-$C_7$-cycloalkyl whose carbon skeleton may be interrupted by one or more nonadjacent —O—, —S—, —$NR^4$—, —$N$=$CR^4$— and/or —$CR^4$=$CR^4$— moieties, where the (het)aryl and cycloalkyl radicals may each be mono- or polysubstituted by $C_1$-$C_{18}$-alkyl and/or the above radicals mentioned as substituents for alkyl;

aryl or hetaryl, to which may be fused further saturated or unsaturated 5- to 7-membered rings whose carbon skeleton may be interrupted by one or more nonadjacent —O—, —S—, —$NR^4$—, —$N$=$CR^4$—, —$CR^4$=$CR^4$—, —CO—, —SO— and/or —$SO_2$— moieties, where the entire ring system may be mono- or polysubstituted by:

$C_1$-$C_{18}$-alkyl, $C_1$-$C_{12}$-alkoxy, $C_1$-$C_6$-alkylthio, —C≡$CR^4$, —$CR^4$=$CR^4{}_2$, hydroxyl, —$NR^5R^6$, —$NR^5COR^6$, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, hydroxyl, $NR^5R^6$ and/or —$NR^5COR^6$;

joined to the nitrogen atom to form a saturated or unsaturated, 5- to 7-membered ring whose carbon chain may be interrupted by one or more nonadjacent —O—, —S— and/or —$NR^4$— moieties, to which may be fused one or two unsaturated or saturated 4- to 8-membered rings whose carbon chain may likewise be interrupted by these nonadjacent moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the above radicals mentioned as substituents for alkyl, or $C_1$-$C_{18}$-alkoxy, $C_1$-$C_{18}$-alkylthio and/or —$NR^5R^6$;

m is 2, 3 or 4;
n is 0, 2 or 4 when m=2 or 3;
    is 0,2, 4 or 6 when m=4; and
p is 0, 2 or 4 when m=2 or 3, where n+p=0, 2 or 4;
    is 0,2, 4 or 6 when m=4, where n+p=0,2, 4 or 6.

2. The material according to claim 1, wherein the variables in formula (I) are each defined as follows:

X are joined together with formation of a six-membered ring to give a radical of the formula (x1), or both are each a —CWWM radical;

Y one of the two radicals is a radical of the formula (y1) or (y2) and the other radical is hydrogen, or they are joined to one another with formation of a six-membered ring to give a radical of the formula (y3);

R are identical or different radicals:
  phenoxy or thiophenoxy, each of which may be mono- or polysubstituted by identical or different (i), (ii), (iii), (iv) and/or (v) radicals:
  (i) $C_1$-$C_{30}$-alkyl whose carbon chain may be interrupted by one or more nonadjacent —O—, —S—, —NR$^4$—, —C≡C—, —CR$^4$=CR$^4$— and/or —CO— and/or —SO$_2$— moieties and which may be mono- or polysubstituted by: $C_1$-$C_{12}$-alkoxy, hydroxyl, halogen, cyano and/or aryl which may be mono- or polysubstituted by $C_1$-$C_{18}$-alkyl or $C_1$-$C_6$-alkoxy;
  (ii) $C_3$-$C_8$-cycloalkyl whose carbon skeleton may be interrupted by one or more nonadjacent —O—, —S—, —NR$^4$—, —CR$^4$=CR$^4$— and/or —CO— moieties and which may be mono- or polysubstituted by $C_1$-$C_{18}$-alkyl, $C_1$-$C_{12}$-alkoxy and/or $C_1$-$C_6$-alkylthio;
  (iii) aryl or hetaryl, to each of which may be fused further 5- to 7-membered saturated or unsaturated rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by:
    $C_1$-$C_{18}$-alkyl, $C_1$-$C_{12}$-alkoxy, —C=CR$^4_2$, —CR$^4$=CR$^4_2$, hydroxyl, halogen, cyano, —NR$^9$R$^{10}$, —NR$^5$COR$^6$, —CONR$^5$R$^6$, —SO$_2$NR$^5$R$^6$, —COOR$^7$, —SO$_3$R$^7$, (het)aryl, (het)aryloxy and/or (het)arylthio, where the (het)aryl radicals may each be mono- or polysubstituted by $C_1$-$C_{18}$-alkyl, $C_1$-$C_{18}$-alkoxy and/or cyano;
  (iv) a —U-aryl radical which may be mono- or polysubstituted by the above radicals mentioned as substituents for the aryl radicals (iii), where U is an —O—, —S—, —NR$^4$—, —CO—, —SO— or —SO$_2$— moiety; and
  (v) $C_1$-$C_{12}$-alkoxy, $C_1$-$C_6$-alkylthio, —C=CR$^4$, —CR$^4$=CR$^4_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$ and/or —SO$_3$R$^7$;

M is hydrogen, an alkali metal cation or [NR$^5$]$_4^+$;
L is a chemical bond or phenylene;
R$^1$, R$^2$ are identical or different phenyl radicals which may each be mono- or polysubstituted by $C_1$-$C_{18}$-alkyl, $C_1$-$C_{12}$-alkoxy, $C_1$-$C_6$-alkyl-thio, —NR$^5$R$^6$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio and/or —NR$^5$R$^6$;
  joined to the nitrogen atom to form a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by: $C_1$-$C_{24}$-alkyl which may be substituted by $C_1$-$C_{18}$-alkoxy, $C_1$-$C_{18}$-alkylthio and/or —NR$^5$R$^6$, (het)aryl which may be mono- or polysubstituted by $C_1$-$C_{18}$-alkyl and/or the above radicals mentioned as substituents for alkyl, $C_1$-$C_{18}$-alkoxy, $C_1$-$C_{18}$-alkylthio and/or —NR$^5$R$^6$;

Z is —O— or —S—;

R$^3$ is $C_1$-$C_{30}$-alkyl whose carbon chain may be interrupted by one or more nonadjacent —O—, —S— and/or —NR$^4$— moieties and which may be mono- or polysubstituted by: $C_1$-$C_{12}$-alkoxy, hydroxyl and/or aryl which may be mono- or polysubstituted by $C_1$-$C_{18}$-alkyl or $C_1$-$C_6$-alkoxy;
  phenyl which may be mono- or polysubstituted by: $C_1$-$C_{18}$-alkyl, $C_1$-$C_{12}$-alkoxy, $C_1$-$C_6$-alkylthio, —NR$^5$R$^6$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio and/or —NR$^5$R$^6$;

R' is $C_6$-$C_{30}$-alkyl whose carbon chain may be interrupted by one or more nonadjacent —O—, —S— and/or —NR$^4$— moieties and which may be mono- or polysubstituted by: $C_1$-$C_6$-alkoxy, $C_1$-$C_6$-alkylthio, —NR$^9$R$^{10}$ and/or aryl which may be mono- or polysubstituted by $C_1$-$C_{18}$-alkyl or $C_1$-$C_6$-alkoxy;
  phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —NR$^9$R$^{10}$, —CONR$^5$R$^6$, —SO$_2$NR$^5$R$^6$ and/or phenoxy, phenylthio, phenylazo and/or naphthylazo, each of which may be substituted by $C_1$-$C_{10}$-alkyl, $C_1$-$C_6$-alkoxy and/or cyano;

R$^4$ is hydrogen or $C_1$-$C_6$-alkyl;

R$^5$, R$^6$ are each independently:
  hydrogen;
  $C_1$-$C_{18}$-alkyl which may be mono- or polysubstituted by $C_1$-$C_6$-alkoxy, hydroxyl, halogen and/or cyano;
  aryl or hetaryl, each of which may be mono- or polysubstituted by $C_1$-$C_6$-alkyl and/or the above radicals mentioned as substituents for alkyl,
  where the R$^5$ radicals may be the same or different when they occur more than once;

R$^7$ is $C_1$-$C_{18}$-alkyl which may be mono- or polysubstituted by $C_1$-$C_6$-alkoxy, hydroxyl, halogen and/or cyano;
  aryl or hetaryl, each of which may be mono- or polysubstituted by $C_1$-$C_6$-alkyl and/or the above radicals mentioned as substituents for alkyl;

R$^9$, R$^{10}$ are each independently $C_1$-$C_{30}$-alkyl whose carbon chain may be interrupted by one or more nonadjacent —O—, —S—, —NR$^4$—, —N=CR$^4$—, —C≡C— and/or —CR$^4$=CR$^4$— moieties and which may be mono- or polysubstituted by:
  $C_1$-$C_{12}$-alkoxy, $C_1$-$C_6$-alkylthio, —C=CR$^4$, —CR$^4$=CR$^4_2$, hydroxyl, —NR$^5$R$^6$, —NR$^5$COR$^6$ and/or (het)aryl which may be mono- or polysubstituted by $C_1$-$C_{18}$-alkyl and/or the above radicals mentioned as substituents for alkyl;
  aryl or hetaryl, to which may be fused further saturated or unsaturated 5- to 7-membered rings whose carbon skeleton may be interrupted by one or more nonadjacent —O—, —S—, —NR$^4$—, —N=CR$^4$—, —CR$^4$=CR$^4$—, —CO—, —SO— and/or —SO$_2$— moieties, where the entire ring system may be mono- or polysubstituted by:
    $C_1$-$C_{18}$-alkyl, $C_1$-$C_{12}$-alkoxy, $C_1$-$C_6$-alkylthio, —C=CR$^4$, —CR$^4$=CR$^4_2$, hydroxyl, —NR$^5$R$^6$, —NR$^5$COR$^6$, (het)aryl, (het)aryloxy and/or (het)

arylthio, where the (het)aryl radicals may each be mono- or polysubstituted by $C_1$-$C_{18}$-alkyl, $C_1$-$C_{12}$-alkoxy, hydroxyl, —$NR^5R^6$ and/or —$NR^5COR^6$;

joined to the nitrogen atom to form a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by $C_1$-$C_{24}$-alkyl which may be substituted by $C_1$-$C_{18}$-alkoxy, $C_1$-$C_{18}$-alkylthio and/or —$NR^5R^6$;

m is 2, 3 or 4;
n is 4 when m=2 or 3;
is 4 or 6 when m=4; and
p is 0.

3. A mixture for producing photoactive layers for solar cells or photodetectors comprising, as components,
  K1) compounds of the general formula (I) according to claim 1 as electron donors or electron acceptors and
  K2) one or more compounds which, with respect to component K1, act correspondingly as electron acceptors or electron donors.

4. A photosensitizer in solar cells or photodetectors comprising a compound of the general formula (I) according to claim 1.

5. A solar cell or photodetector comprising compounds of the general formula (I) according to claim 1.

* * * * *